United States Patent
Deans

(10) Patent No.: US 12,139,724 B2
(45) Date of Patent: *Nov. 12, 2024

(54) METHODS OF MAKING RED BLOOD CELLS AND PLATELETS IN VITRO AND USES THEREOF

(71) Applicant: University of Utah Research Foundation, Salt Lake City, UT (US)

(72) Inventor: Tara L. Deans, Cottonwood Heights, UT (US)

(73) Assignee: University of Utah Research Foundation, Salt Lake City, UT (US)

(*) Notice: Subject to any disclaimer, the term of this patent is extended or adjusted under 35 U.S.C. 154(b) by 0 days.

This patent is subject to a terminal disclaimer.

(21) Appl. No.: 17/721,690

(22) Filed: Apr. 15, 2022

(65) Prior Publication Data

US 2022/0251510 A1     Aug. 11, 2022

Related U.S. Application Data

(63) Continuation of application No. 15/745,305, filed as application No. PCT/US2016/042084 on Jul. 13, 2016, now Pat. No. 11,319,528.

(60) Provisional application No. 62/231,690, filed on Jul. 13, 2015.

(51) Int. Cl.
| | |
|---|---|
| C12N 5/078 | (2010.01) |
| C12N 5/074 | (2010.01) |
| C12N 5/0789 | (2010.01) |
| C12N 15/85 | (2006.01) |

(52) U.S. Cl.
CPC ......... *C12N 5/0644* (2013.01); *C12N 5/0641* (2013.01); *C12N 5/0647* (2013.01); *C12N 15/85* (2013.01); *C12N 5/0696* (2013.01); *C12N 2501/14* (2013.01); *C12N 2501/145* (2013.01); *C12N 2510/00* (2013.01)

(58) Field of Classification Search
CPC .. C12N 5/0644; C12N 5/0641; C12N 5/0647; C12N 15/85; C12N 5/0696; C12N 2501/14; C12N 2501/145; C12N 2510/00
USPC .......................................................... 435/372
See application file for complete search history.

(56) References Cited

U.S. PATENT DOCUMENTS

| | | | |
|---|---|---|---|
| 7,696,168 B2 | 4/2010 | Kuliopulos et al. | |
| 9,982,034 B2 | 5/2018 | Wilcox et al. | |
| 2005/0053587 A1 | 3/2005 | Galipeau et al. | |
| 2007/0243608 A1 | 10/2007 | Kyba et al. | |
| 2010/0175141 A1 | 7/2010 | Collins et al. | |
| 2011/0256626 A1 | 10/2011 | Park et al. | |
| 2013/0274129 A1 | 10/2013 | Katzen et al. | |
| 2014/0024118 A1 | 1/2014 | Nakamura et al. | |
| 2014/0086883 A1 | 3/2014 | Poncz et al. | |
| 2014/0315753 A1 | 10/2014 | Guye et al. | |
| 2014/0363455 A1 | 12/2014 | Stull et al. | |
| 2018/0273980 A1 | 9/2018 | Qi et al. | |
| 2019/0048317 A1 | 2/2019 | Eto et al. | |

FOREIGN PATENT DOCUMENTS

| | | |
|---|---|---|
| AU | 2019354370 | 3/2021 |
| CA | 3115104 | 3/2021 |
| EP | 16825107.2 | 7/2016 |
| EP | 2019868626 | 5/2021 |
| IL | 282003 | 4/2021 |
| JP | 2021518797 | 4/2021 |
| KR | 1020217013329 | 5/2021 |
| WO | WO-1999/43809 A2 | 9/1999 |
| WO | WO-2003/072755 A2 | 9/2003 |
| WO | WO-2009/137629 A2 | 11/2009 |
| WO | PCT/US2016/042084 | 7/2016 |
| WO | WO-2017/011550 A1 | 1/2017 |
| WO | WO-2017/132580 A2 | 8/2017 |
| WO | PCT/US2019/054032 | 10/2019 |
| WO | PCT/US2020/053445 | 9/2020 |

OTHER PUBLICATIONS

Abe, T. et al., Effect of recombinant erythropoietin in interaction with stromal factors on cord blood hematopoiesis. Blood. 1996; 87(8):3212-7.
Antonchuk, J. et al., HOXB4-induced expansion of adult hematopoietic stem cells ex vivo. Cell. 2002; 109(1):39-45.
Assou, S. et al., Dynamic changes in gene expression during human early embryo development: from fundamental aspects to clinical applications. Hum Reprod Update. 2011; 17(2):272-90 (33 pages).
Aulehla, A. and Pourquie, O., Oscillating signaling pathways during embryonic development. Curr Opin Cell Biol. 2008; 20(6):632-7.
Becskei, A. and Serrano, L., Engineering stability in gene networks by autoregulation. Nature. 2000; 405(6786):590-3.
Bouhassira, E.E., Concise Review: Production of Cultured Red Blood Cells from Stem Cells. Stem Cells Transl Med. 2012; 1(12):927-33.
Casola, S., Mouse Models for miRNA Expression: the ROSA26 Locus. Methods Mol Biol. 2010; 667:145-63.
Chang, Y. et al., From hematopoietic stem cells to platelets, J Thromb Haemost. 2007; 5(Suppl 1):318-27.
Chen, C.-Y.A. et al., Versatile applications of transcriptional pulsing to study mRNA turnover in mammalian cells. RNA. 2007; 13(10):1775-86.
Chen, H.-W. et al., Dynamic changes of gene expression profiles during postnatal development of the heart in mice. Heart. 2004; 90(8):927-34.
Chen, Y.Y. et al., Genetic control of mammalian T-cell proliferation with synthetic RNA regulatory systems. Proc natl Acad Sci USA. 2010; 107:8531-6.

(Continued)

*Primary Examiner* — Jennifer M. H. Tichy
(74) *Attorney, Agent, or Firm* — Ballard Spahr LLP

(57) ABSTRACT

Disclosed herein are methods of producing platelets and red blood cells using synthetic biology and uses thereof. The methods disclosed herein can also be used to produce platelets and red blood cells comprising a therapeutic agent. The cells produced by the methods disclosed herein can be used to treat, manage, prevent and diagnosis various diseases and disorders and be used as a research tool.

14 Claims, 20 Drawing Sheets

Specification includes a Sequence Listing.

(56) References Cited

OTHER PUBLICATIONS

Chin, J.W., Programming and engineering biological networks. Curr Opin Struct Biol. 2006; 16:551-6.
Chubb, J.R. et al., Transcriptional pulsing of a developmental gene. Curr Biol. 2006; 16(10):1018-25 (14 pages).
Cid, J. and Lozano, M., Platelet dose for prophylactic platelet transfusions. Expert Rev Hematol. 2010; 3(4):397-400.
Corum, L.E. and Hlady, V., Screening platelet-surface interactions using negative surface charge gradients. Biomaterials. 2010; 31(12):3148-55.
Corum, L.E. and Hlady, V., The effect of upstream platelet-fibrinogen interactions on downstream adhesion and activation. Biomaterials. 2012; 33(5):1255-60 (14 pages).
Deans, T.L. et al., A Tunable Genetic Switch Based on RNAi and Repressor Proteins for Regulating Gene Expression in Mammalian Cells. Cell. 2007; 130(2):363-72.
Deans, T.L. et al., Regulating synthetic gene networks in 3D materials. Proc Natl Acad Sci USA. 2012; 109(38):15217-22.
Deutsch, V.R. and Tomer, A., Megakaryocyte development and platelet production. Br J Haematol. 2006; 134(5):453-66.
El Golli, N. et al., Evidence for a granule targeting sequence within platelet factor 4. J Biol Chem. 2005; 280(34):30329-35.
Elowitz, M.B. and Leibler, S., A synthetic oscillatory network of transcriptional regulators. Nature. 2000; 403(6767):335-8.
Feng, Q. et al., Scalable generation of universal platelets from human induced pluripotent stem cells. Stem Cell Reports. 2014; 3:817-31.
Friedland, A.E., et al., Synthetic gene networks that count. Science. 2009; 324:1199-202.
Fugger, L. et al., From genes to function: the next challenge to understanding multiple sclerosis. Nat Rev Immunol. 2009; 9(6):408-17.
Fujimoto, T.T. et al., Production of functional platelets by differentiated embryonic stem (ES) cells in vitro. Blood. 2003; 102(12):4044-51.
Gardner, T.S. et al., Construction of a genetic toggle switch in *Escherichia coli*. Nature. 2000; 403:339-42.
Grayson, W.L. et al., Effects of initial seeding density and fluid perfusion rate on formation of tissue-engineered bone. Tissue Eng Part A. 2008; 14(11):1809-20. (19 pages).
Grover, A. et al., Erythropoietin guides multipotent hematopoietic progenitor cells toward an erythroid fate. J Exper Med. 2014; 211:181-8.
Gutiérrez, L. et al., Ablation of Gata1 in adult mice results in aplastic crisis, revealing its essential role in steady-state and stress erythropoiesis. Blood. 2008; 111(8):4375-85.
Handwerger, S. and Aronow, B., Dynamic changes in gene expression during human trophoblast differentiation. Recent Prog Horm Res. 2003; 58:263-81.
Haugh, M.G. et al., Temporal and spatial changes in cartilage-matrix-specific gene expression in mesenchymal stem cells in response to dynamic compression. Tissue Eng Part A. 2011; 17(23-24):3085-93 (13 pages).
Hippenmeyer, S. et al., Genetic mosaic dissection of Lis1 and Ndel1 in neuronal migration. Neuron. 2010; 68(4):695-709 (27 pages).
Holland, A.J. et al., Inducible, Reversible System for the Rapid and Complete Degradation of Proteins in Mammalian Cells. Proc Natl Acad Sci USA. 2012; 109(49):E3350-7.
Holmes, ML et al. "Cloning and Analysis of the Thrombopoietin-induced Megakaryocyte-specific Glycoprotein VI Promoter and Its Regulation by GATA-1, F11-1, and Sp1", The Journal of Biological Chemistry. Dec. 13, 2002, vol. 277, No. 50, pp. 48333-48341.
Iwasaki, H. et al., GATA-1 converts lymphoid and myelomonocytic progenitors into the megakaryocyte/erythrocyte lineages. Immunity. 2003; 19(3):451-62.
Iyer-Biswas, S. et al., Stochasticity of gene products from transcriptional pulsing. Phys Rev E Stat Nonlin Soft Matter Phys. 2009; 79(3 Pt 1):031911 (9 pages).
Katzman, R.L. et al., Collagen-induced platelet aggregation: involvement of an active glycopeptide fragment (alpha1-CB5). Science. 1973; 181(4100):670-2.
Kaufman, R.M. et al., Circulating megakaryocytes and platelet release in the lung. Blood. 1965; 26(6):720-31.
Klimchenko, O. et al., A common bipotent progenitor generates the erythroid and megakaryocyte lineages in embryonic stem cell-derived primitive hematopoiesis. Blood. 2009; 114:1506-17.
Kotula, J.W. et al., Programmable bacteria detect and record an environmental signal in the mammalian gut. Proc Natl Acad Sci USA. 2014; 111:4838-43.
Kuter, D.J. et al., Evaluation of bone marrow reticulin formation in chronic immune thrombocytopenia patients treated with romiplostim. Blood. 2009; 114(18):3748-56.
Kuter, D.J., Biology and chemistry of thrombopoietic agents. Semin Hematol. 2010; 47:243-8 (13 pages).
Kyba, M. et al., HoxB4 confers definitive lymphoid-myeloid engraftment potential on embryonic stem cell and yolk sac hematopoietic progenitors. Cell. 2002; 109(1):29-37.
Lo, M.Y. et al., Rapid transcriptional pulsing dynamics of high expressing retroviral transgenes in embryonic stem cells. PloS One. 2012; 7(5):e37130 (13 pages).
Lu, S.-J. et al., Platelets generated from human embryonic stem cells are functional in vitro and in the microcirculation of living mice. Cell Res. 2011; 21:530-45.
Lu, T.K. et al., Next-generation synthetic gene networks. Nat Biotechnol. 2009; 27:1139-50.
Machlus, K.R. and Italiano, J.E., Jr., The incredible journey: From megakaryocyte development to platelet formation. J Cell Biol. 2013; 201:785-96.
Messerle, M. et al., Dynamic changes in gene expression during in vitro differentiation of mouse embryonic stem cells. Cytokines Mol Ther. 1995; 1(2):139-43.
Metcalf, D., Hematopoietic cytokines. Blood. 2008; 111:485-91.
Mikhailidis, D.P. et al., Fibrinogen mediated activation of platelet aggregation and thromboxane A2 release: pathological implications in vascular disease. J Clin Pathol. 1985; 38(10):1166-71.
Miller, J.L. et al., von Willebrand factor binds to platelets and induces aggregation in platelet-type but not type IIB von Willebrand disease. J Clin Invest. 1983; 72(5):1532-42.
Mok, P.-L. et al., In vitro expression of erythropoietin by transfected human mesenchymal stromal cells. Cytotherapy. 2008; 10(2):116-24.
Mosaad, Y.M., Hematopoietic stem cells: an overview. Transfus Apher Sci. 2014; 51(3): 68-82.
Muggli, R., Collagen-induced platelet aggregation: native collagen quaternary structure is not an essential structural requirement. Thromb Res. 1978; 13(5):829-43.
Mukherji, S. and van Oudenaarden, A., Synthetic biology: understanding biological design from synthetic circuits. Nat Rev Genet. 2009; 10(12):859-71 (28 pages).
NHLBI, Stem Cell-Derived Blood Products for Therapeutic Use, RFA-HL-15-022 (2014) (20 pages).
Nishimura, K. et al., An auxinbased degron system for the rapid depletion of proteins in nonplant cells. Nat Methods. 2009; 6(12):917-22.
Olsen, A.L., Designer Blood: Creating Hematopoetic Lineages from Embryonic Stem Cells. Blood. 2006; 107(4):1265-75.
Ono, Y. et al., Induction of functional platelets from mouse and human fibroblasts by p45NFE2/Maf. Blood. 2012; 120(18):3812-21 (21 pages).
Orkin, S.H. and Zon, L.I., Hematopoiesis: an evolving paradigm for stem cell biology. Cell. 2008; 132(4):631-44 (26 pages).
Potter, C.J. et al., The Q system: a repressible binary system for transgene expression, lineage tracing, and mosaic analysis. Cell. 2010; 141(3):536-48 (24 pages).
Ramakrishnan, V. et al., A thrombin receptor function for platelet glycoprotein Ib-IX unmasked by cleavage of glycoprotein V. Proc Natl Acad Sci USA. 2001; 98(4):1823-8.
Rhee, J.M et al., In vivo imaging and differential localization of lipid-modified GFP-variant fusions in embryonic stem cells and mice. Genesis. 2006; 44(4):202-18 (25 pages).

(56) References Cited

OTHER PUBLICATIONS

Robert, A. et al., Megakaryocyte and platelet production from human cord blood stem cells. Methods Mol Biol. 2012; 788:219-47.
Siuti,P. et al., Synthetic circuits integrating logic and memory in living cells. Nature Biotechnol. 2013; 31:448-52.
Slusarczyk, A.L. et al., Foundations for the design and implementation of synthetic genetic circuits. Nature Rev. Genetics. 2012; 13(6):406-20.
Sternberg, N. and Hamilton, D., Bacteriophage P1 site-specific recombination. I. Recombination between loxP sites. J Mol Biol. 1981; 150(4):467-86.
Stetler-Stevenson, M. et al., Diagnostic utility of flow cytometric immunophenotyping in myelodysplastic syndrome. Blood. 2001; 98(4):79-87.
Subedi, A. et al., Adoption of the Q transcriptional regulatory system for zebrafish transgenesis. Methods. 2014; 66(3):433-40 (19 pages).
Suzuki, N. et al., Oscillatory protein expression dynamics endows stem cells with robust differentiation potential. PloS One. 2011; 6(11):e27232 (15 pages).
Suzuki, M. et al., Differential Contribution of the Gata1 Gene Hematopoietic Enhancer to Erythroid Differentiation. Mol Cell Biol. 2009; 29(5):1163-75.
Takayama, N. et al., Generation of functional platelets from human embryonic stem cells in vitro via ES-sacs, VEGF-promoted structures that concentrate hematopoietic progenitors. Blood. 2008; 111(11):5298-306.
Tasic, B. et al., Site-specific integrase-mediated transgenesis in mice via pronuclear injection. Proc Natl Acad Sci USA. 2011; 108:7902-7.
Ungerer, M. et al., Generation of functional culture-derived platelets from CD34+ progenitor cells to study transgenes in the platelet environment. Circ Res. 2004; 95(5):e36-44.
Westrick, R.J. et al., Murine models of vascular thrombosis (Eitzman series). Arterioscler Thromb Vasc Biol. 2007; 27(10):2079-93.
Wu, N. et al., Comparison of mouse matrix metalloproteinase 13 expression in free-electron laser and scalpel incisions during wound healing. J Invest Dermatol. 2003; 121(4):926-32.
Xie, Z. et al., Multi-input RNAi-Based Logic Circuit for Identification of Specific Cancer Cells. Science. 2011; 333(6047):1307-11.
Ye, H. and Fussenegger, M., Synthetic Therapeutic Gene Circuits in Mammalian Cells. FEBS Letters. 2014; 588(15):2537-44.
Ye, H. et al., A synthetic optogenetic transcription device enhances blood-glucose homeostasis in mice. Science. 2011; 332(6037):1565-8.
Zon, L.I., Intrinsic and extrinsic control of haematopoietic stem-cell self-renewal. Nature. 2008; 453(7193):306-13.
Zhang, C et al. "Activation of the Megakaryocyte-specific Gene Platelet Basic Protein (PBP) by the Ets Family Factor PU.1.", The Journal of Biological Chemistry. Oct. 17, 1997, vol. 272, No. 42, pp. 26236-26246.
International Search Report and Written Opinion were mailed on Dec. 27, 2019 by the International Searching Authority for International Application No. PCT/US2019/054032, filed on Oct. 1, 2019 (Applicant—University of Utah Research Foundation) (25 Pages).
International Search Report and Written Opinion mailed on Oct. 28, 2016 by the International Searching Authority for Patent Application No. PCT/US2016/042084, which was filed on Jul. 13, 2016 and published as WO 2017/011550 on Jan. 19, 2017 (Inventor—Tara L. Deans; Applicant—University of Utah Research Foundation) (19 pages).
International Preliminary Report on Patentability issued on Jan. 16, 2018 by the International Searching Authority for Patent Application No. PCT/US2016/042084, which was filed on Jul. 13, 2016 and published as WO 2017/011550 on Jan. 19, 2017 (Inventor—Tara L. Deans; Applicant—University of Utah Research Foundation) (17 pages).
Supplementary European Search Report and Written Opinion issued on Apr. 1, 2019 by the European Patent Office for Patent Application No. 16825107.2, which was filed on Jul. 13, 2016 and published as EP 3322800 on May 23, 2018 (Inventor—Tara L. Deans; Applicant—University of Utah Reserach Foundation) (8 pages).
International Search Report and Written Opinion were mailed on Feb. 9, 2021 by the International Searching Authority for International Application No. PCT/US2020/053445, filed on Sep. 30, 2020 (Applicant—University of Utah Research Foundation) (15 Pages).
U.S. Appl. No. 62/231,690, filed Jul. 13, 2015, Tara L. Deans (Univ. of Utah Res. Found.).
U.S. Appl. No. 15/745,305 (U.S. Pat. No. 11,319,528), Jan. 16, 2018 (Jan. 10, 2019), Tara L. Deans (Univ. of Utah Res. Found.).
U.S. Appl. No. 62/741,971, filed Oct. 5, 2018, Tara L. Deans (Univ. of Utah Res. Found.).
U.S. Appl. No. 17/280,415 (2022-0033776), Mar. 26, 2021 (Feb. 2, 2022), Tara L. Deans (Univ. of Utah Res. Found.).
U.S. Appl. No. 62/908,874, filed Oct. 1, 2019, Tara L. Deans (Univ. of Utah Res. Found.).
U.S. Appl. No. 17/765,872, filed Apr. 1, 2022, Tara L. Deans (Univ. of Utah Res. Found.).

METHODS OF MAKING RED BLOOD CELLS AND PLATELETS IN VITRO AND USES THEREOF

CROSS REFERENCE TO RELATED APPLICATIONS

This application is a continuation of U.S. application Ser. No. 15/745,305 (now U.S. Pat. No. 11,319,528) filed on Jan. 16, 2018, which claims the benefit of priority under 35 U.S.C. § 371 of International Application No. PCT/US2016/042084, filed on Jul. 13, 2016, which claims the benefit of the filing date of U.S. Provisional Application No. 62/231,690, which was filed on Jul. 13, 2015. The content of these earlier filed applications is hereby incorporated by reference herein in its entirety.

REFERENCE TO SEQUENCE LISTING

The sequence listing submitted herewith as a text filed named "21101_0322U3_SL," created on Apr. 15, 2022, and having a size of 473 bytes is herein incorporated by reference in its entirety pursuant to 37 C.F.R. § 1.52(e)(5).

BACKGROUND

A priority outlined by the National Heart, Lung and Blood Institute is to develop and further enhance tools and techniques for regulating stem cell differentiation and maturation to efficiently produce functional stem cell-derived products that lack a nucleus: specifically platelets and red blood cells (RBCs) in an efficient and cost effective manner. Platelets are important for hemostasis, and thrombocytopenia (e.g., low platelet counts) is a major clinical problem associated with many conditions including idiopathic thrombocytopenic purpura (ITP), myelodysplastic syndromes, chemotherapy, aplastic anemia, HIV infection, surgery, and complications during pregnancy. It is estimated that about 1.5 million platelet transfusions are administered each year to prevent severe bleeding and the source of these platelets are human donors.

SUMMARY

Described herein are methods for developing an in vitro source of platelets and red blood cells using technologies based upon emerging advances in the field of synthetic biology. This approach is significant because it has the potential to produce large volumes of purified platelets and possibly from autologous sources. Moreover, in vitro production of these cells minimizes the risks associated with human donation.

Disclosed herein are methods of producing red blood cells or platelets, the method comprising: a) providing a genetically engineered feeder cell, wherein the feeder cell comprises one or more genetic circuits, wherein the one or more genetic circuits comprise one or more genes of interest; and one or more promoters; b) providing a genetically engineered fed cell, wherein the fed cell comprises one or more genetic circuits, wherein the one or more genetic circuits comprise one or more genes of interest, wherein the one or more genes of interest are different than the one or more genes of interest in a); and one or more promoters; and c) culturing the genetically engineered feeder cell in a) with the genetically engineered fed cell in b) in a media under conditions that permit the genetically engineered fed cells to differentiate into red blood cells or platelets; wherein one or more of the genetically engineered fed cells differentiate into red blood cells or platelets.

Disclosed herein are methods of producing platelets or red blood cells comprising a therapeutic agent, the method comprising a) providing a genetically engineered feeder cell, wherein the feeder cell comprises one or more genetic circuits; wherein the one or more genetic circuits comprise one or more genes of interest; and one or more promoters; b) providing a genetically engineered fed cell, wherein the fed cell comprises one or more genetic circuits; wherein the one or more genetic circuits comprise one or more genes of interest, wherein the one or more genes of interest are different than the one or more genes of interest in a); and one or more promoters; c) culturing the genetically engineered feeder cell in a) with the genetically engineered fed cell in b) in a media under conditions that permit the genetically engineered fed cells to differentiate into platelet and/or red blood cell progenitor stem cells; and d) producing the platelet or red blood cells comprising a therapeutic agent.

BRIEF DESCRIPTION OF THE DRAWINGS

FIG. 1A is a schematic of the Q repressible binary expression system. In the absence of the transcription factor, QF, EGFP is not expressed. FIG. 1B shows that when an RNAi target is placed in the 3' UTR, post-transcriptional knockdown is achieved to knockdown any transcriptional leakage. FIG. 1C shows that when QF and QUAS_EGFP are both present, QF binds to QUAS and activates gene expression. FIG. 1D shows that when QS, QF, and QUAS_EGFP are present in the same cell, QS represses QF and EGFP is not expressed. Inhibition can be alleviated by the addition of QA, which binds to QS and allows QF to activate EGFP. FIG. 1E is flow cytometry results showing level of EGFP gene expression.

FIG. 2A shows that expressing transport inhibitor response 1 protein (TIR1) along with an AID-tagged protein has no effect on protein expression. FIG. 2B shows auxin binding to TIR1 promotes the interaction between TIR1 and AID resulting in the degradation of the target protein (GFP).

FIG. 5A shows, using CRISPR/Cas9 technology, the addition of three attP sites to the Rosa26 locus. FIG. 5B illustrates the unidirectional recombination at the attP sites to insert genetic circuits at the Rosa26 locus.

FIG. 10A shows Cre is off in the absence of an inducer, i) allowing for EPO to be expressed. FIG. 10B shows that in the presence of an inducer, Cre is turned on, causing ii) a homologous recombination at the LoxP sites, removing the EPO gene. FIG. 10C shows the predicted gene expression output.

FIG. 11A shows EPO is off in the absence of an inducer. FIG. 11B shows that in the presence of an inducer, EPO is turned on and can be controlled to i) tune the level of EPO expression, or ii) oscillate its expression. Thrombopoietin (TPO) is constitutively expressed in both cases. FIG. 11C shows the predicted gene expression output.

FIG. 12A shows that EPO is turned on in the presence of IPTG to i) tune its level of expression or ii) oscillate its expression. FIG. 12B shows that TPO is turned on in the presence of QA to i) tune its level of expression or ii) oscillate its expression. FIG. 12C shows the predicted gene expression output.

FIG. 14A shows Cre is off in the absence of an inducer, i) allowing for HoxB4 to be expressed; GATA-1 is not expressed. FIG. 14B shows that in the presence of an inducer, Cre is turned on, causing ii) a homologous recombination at the LoxP sites, removing the HoxB4 gene and shifting GATA-1 into frame to be expressed. FIG. 14C shows the predicted gene expression output.

FIG. 15A shows that Cre is off in the absence of IPTG. FIG. 15B shows that in the presence of IPTG, Cre is turned on causing homologues recombination at the LoxP sites, removing HoxB4 and turning on GATA-1. FIG. 15C shows that adding auxin allows for the rapid degradation of GATA-1 protein, allowing for control of its protein products (i-iii).

DETAILED DESCRIPTION

Figures 1A, 1B, 1C, 1D, 1E:
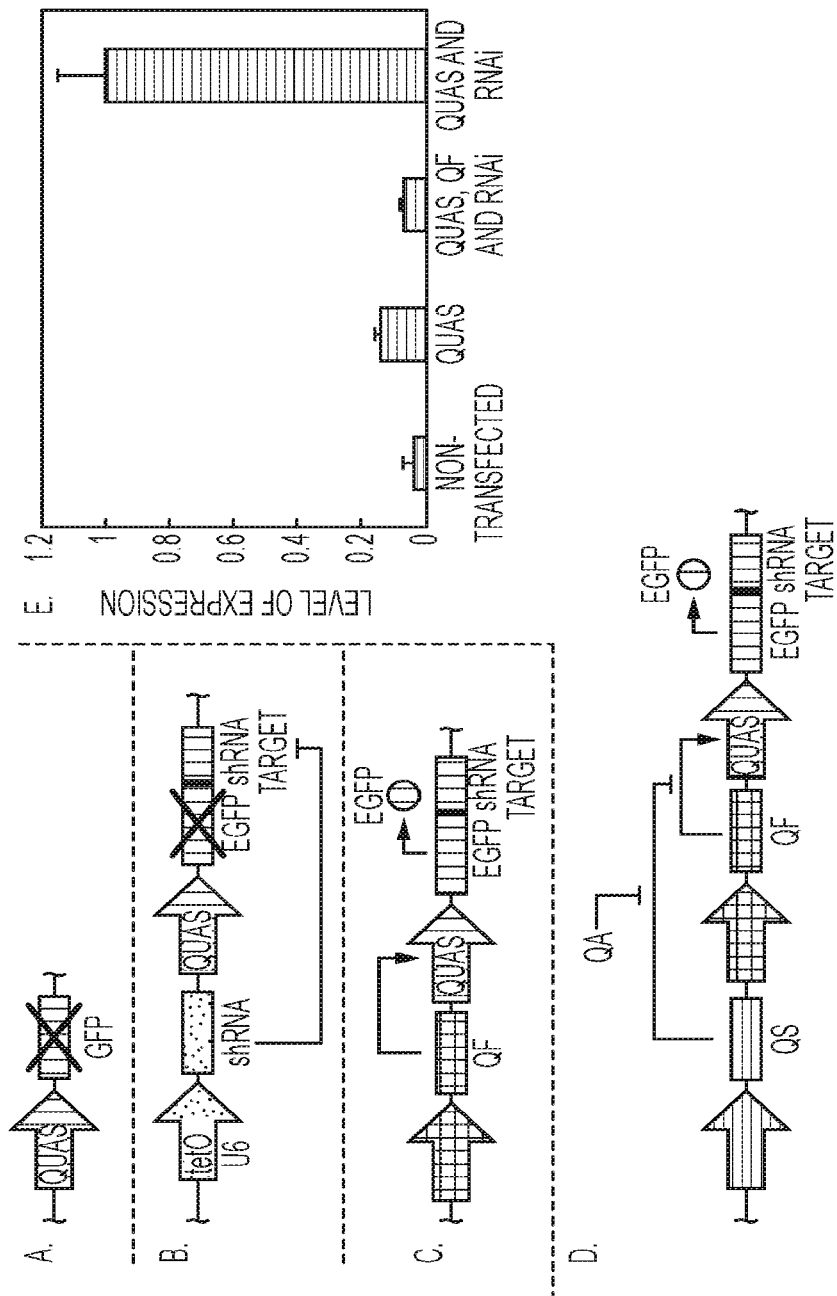
FIGS. 1A-E illustrates the Q-system in mammalian cells.

The present disclosure can be understood more readily by reference to the following detailed description of the invention, the figures and the examples included herein.

Before the present methods and compositions are disclosed and described, it is to be understood that they are not limited to specific synthetic methods unless otherwise specified, or to particular reagents unless otherwise specified, as such may, of course, vary. It is also to be understood that the terminology used herein is for the purpose of describing particular aspects only and is not intended to be limiting. Although any methods and materials similar or equivalent to those described herein can be used in the practice or testing of the present invention, example methods and materials are now described.

Moreover, it is to be understood that unless otherwise expressly stated, it is in no way intended that any method set forth herein be construed as requiring that its steps be performed in a specific order. Accordingly, where a method claim does not actually recite an order to be followed by its steps or it is not otherwise specifically stated in the claims or descriptions that the steps are to be limited to a specific order, it is in no way intended that an order be inferred, in any respect. This holds for any possible non-express basis for interpretation, including matters of logic with respect to arrangement of steps or operational flow, plain meaning derived from grammatical organization or punctuation, and the number or type of aspects described in the specification.

All publications mentioned herein are incorporated herein by reference to disclose and describe the methods and/or materials in connection with which the publications are cited. The publications discussed herein are provided solely for their disclosure prior to the filing date of the present application. Nothing herein is to be construed as an admission that the present invention is not entitled to antedate such publication by virtue of prior invention. Further, the dates of publication provided herein can be different from the actual publication dates, which can require independent confirmation.

Definitions

As used in the specification and the appended claims, the singular forms "a," "an" and "the" include plural referents unless the context clearly dictates otherwise.

The word "or" as used herein means any one member of a particular list and also includes any combination of members of that list.

Ranges can be expressed herein as from "about" or "approximately" one particular value, and/or to "about" or "approximately" another particular value. When such a range is expressed, a further aspect includes from the one particular value and/or to the other particular value. Similarly, when values are expressed as approximations, by use of the antecedent "about," or "approximately," it will be understood that the particular value forms a further aspect. It will be further understood that the endpoints of each of the ranges are significant both in relation to the other endpoint and independently of the other endpoint. It is also understood that there are a number of values disclosed herein and that each value is also herein disclosed as "about" that particular value in addition to the value itself. For example, if the value "10" is disclosed, then "about 10" is also disclosed. It is also understood that each unit between two particular units is also disclosed. For example, if 10 and 15 are disclosed, then 11, 12, 13, and 14 are also disclosed.

As used herein, the terms "optional" or "optionally" mean that the subsequently described event or circumstance may or may not occur and that the description includes instances where said event or circumstance occurs and instances where it does not.

As used herein, the term "sample" is meant a tissue or organ from a subject; a cell (either within a subject, taken directly from a subject, or a cell maintained in culture or from a cultured cell line); a cell lysate (or lysate fraction) or cell extract; or a solution containing one or more molecules derived from a cell or cellular material (e.g. a polypeptide or nucleic acid), which is assayed as described herein. A sample may also be any body fluid or excretion (for example, but not limited to, blood, urine, stool, saliva, tears, bile) that contains cells or cell components.

As used herein, the term "subject" refers to the target of administration, e.g., a human. Thus the subject of the disclosed methods can be a vertebrate, such as a mammal, a fish, a bird, a reptile, or an amphibian. The term "subject" also includes domesticated animals (e.g., cats, dogs, etc.), livestock (e.g., cattle, horses, pigs, sheep, goats, etc.), and laboratory animals (e.g., mouse, rabbit, rat, guinea pig, fruit fly, etc.). In one aspect, a subject is a mammal. In another aspect, a subject is a human. The term does not denote a particular age or sex. Thus, adult, child, adolescent and newborn subjects, as well as fetuses, whether male or female, are intended to be covered.

As used herein, the term "patient" refers to a subject afflicted with a disease or disorder. The term "patient" includes human and veterinary subjects. In some aspects of the disclosed methods, the "patient" has been diagnosed with a need for treatment for cancer, such as, for example, prior to the administering step.

As used herein, the term "comprising" can include the aspects "consisting of" and "consisting essentially of."

The term "vector" or "construct" refers to a nucleic acid sequence capable of transporting into a cell another nucleic acid to which the vector sequence has been linked. The term "expression vector" includes any vector, (e.g., a plasmid, cosmid or phage chromosome) containing a gene construct in a form suitable for expression by a cell (e.g., linked to a transcriptional control element). "Plasmid" and "vector" are used interchangeably, as a plasmid is a commonly used form of vector. Moreover, the invention is intended to include other vectors which serve equivalent functions.

The term "expression vector" is herein to refer to vectors that are capable of directing the expression of genes to which they are operatively-linked. Common expression vectors of utility in recombinant DNA techniques are often in the form of plasmids. Recombinant expression vectors can comprise a nucleic acid as disclosed herein in a form suitable for expression of the acid in a host cell. In other words, the recombinant expression vectors can include one or more regulatory elements or promoters, which can be selected based on the host cells used for expression that is operatively linked to the nucleic acid sequence to be expressed.

The term "sequence of interest" or "gene of interest" can mean a nucleic acid sequence (e.g., a therapeutic gene), that is partly or entirely heterologous, i.e., foreign, to a cell into which it is introduced.

The term "sequence of interest" or "gene of interest" can also mean a nucleic acid sequence, that is partly or entirely homologous to an endogenous gene of the cell into which it is introduced, but which is designed to be inserted into the genome of the cell in such a way as to alter the genome (e.g., it is inserted at a location which differs from that of the natural gene or its insertion results in "a knockout"). For example, a sequence of interest can be cDNA, DNA, or mRNA.

The term "sequence of interest" or "gene of interest" can also mean a nucleic acid sequence that is partly or entirely complementary to an endogenous gene of the cell into which it is introduced.

A "sequence of interest" or "gene of interest" can also include one or more transcriptional regulatory sequences and any other nucleic acid, such as introns, that may be necessary for optimal expression of a selected nucleic acid. A "protein of interest" means a peptide or polypeptide sequence (e.g., a therapeutic protein), that is expressed from a sequence of interest or gene of interest.

The term "operatively linked to" refers to the functional relationship of a nucleic acid with another nucleic acid sequence. Promoters, enhancers, transcriptional and translational stop sites, and other signal sequences are examples of nucleic acid sequences operatively linked to other sequences. For example, operative linkage of DNA to a transcriptional control element refers to the physical and functional relationship between the DNA and promoter such that the transcription of such DNA is initiated from the promoter by an RNA polymerase that specifically recognizes, binds to and transcribes the DNA.

"Inhibit," "inhibiting" and "inhibition" mean to diminish or decrease an activity, response, condition, disease, or other biological parameter. This can include, but is not limited to, the complete ablation of the activity, response, condition, or disease. This may also include, for example, a 10% inhibition or reduction in the activity, response, condition, or disease as compared to the native or control level. Thus, in an aspect, the inhibition or reduction can be a 10, 20, 30, 40, 50, 60, 70, 80, 90, 100%, or any amount of reduction in between as compared to native or control levels. In an aspect, the inhibition or reduction is 10-20, 20-30, 30-40, 40-50, 50-60, 60-70, 70-80, 80-90, or 90-100% as compared to native or control levels. In an aspect, the inhibition or reduction is 0-25, 25-50, 50-75, or 75-100% as compared to native or control levels.

"Modulate", "modulating" and "modulation" as used herein mean a change in activity or function or number. The change may be an increase or a decrease, an enhancement or an inhibition of the activity, function or number.

The terms "alter" or "modulate" can be used interchangeable herein referring, for example, to the expression of a nucleotide sequence in a cell means that the level of expression of the nucleotide sequence in a cell after applying a method as described herein is different from its expression in the cell before applying the method.

"Promote," "promotion," and "promoting" refer to an increase in an activity, response, condition, disease, or other biological parameter. This can include but is not limited to the initiation of the activity, response, condition, or disease. This may also include, for example, a 10% increase in the activity, response, condition, or disease as compared to the native or control level. Thus, in an aspect, the increase or promotion can be a 10, 20, 30, 40, 50, 60, 70, 80, 90, 100%, or more, or any amount of promotion in between compared to native or control levels. In an aspect, the increase or promotion is 10-20, 20-30, 30-40, 40-50, 50-60, 60-70, 70-80, 80-90, or 90-100% as compared to native or control levels. In an aspect, the increase or promotion is 0-25, 25-50, 50-75, or 75-100%, or more, such as 200, 300, 500, or 1000% more as compared to native or control levels. In an aspect, the increase or promotion can be greater than 100 percent as compared to native or control levels, such as 100, 150, 200, 250, 300, 350, 400, 450, 500% or more as compared to the native or control levels.

As used herein, "CRISPR system" and "CRISPR-Cas system" refers to transcripts and other elements involved in the expression of or directing the activity of CRISPR-associated ("Cas") genes, including sequences encoding a Cas gene, a guide sequence (also referred to as a "spacer" in the context of an endogenous CRISPR system; e.g. guide RNA or gRNA), or other sequences and transcripts from a CRISPR locus. In some aspects, one or more elements of a CRISPR system is derived from a type I, type II, or type III CRISPR system. In some aspects, one or more elements of a CRISPR system are derived from a particular organism comprising an endogenous CRISPR system, such as *Streptococcus pyogenes*. Generally, a CRISPR system is characterized by elements that promote the formation of a CRISPR complex at the site of a target sequence (also referred to as a proto spacer in the context of an endogenous CRISPR system).

As used herein, the terms "disease" or "disorder" or "condition" are used interchangeably referring to any alternation in state of the body or of some of the organs, interrupting or disturbing the performance of the functions and/or causing symptoms such as discomfort, dysfunction, distress, or even death to the person afflicted or those in contact with a person. A disease or disorder or condition can also related to a distemper, ailing, ailment, malady, disorder, sickness, illness, complaint, or affection.

As used herein, the terms "promoter," "promoter element," or "promoter sequence" are equivalents and as used herein, refers to a DNA sequence which when operatively linked to a nucleotide sequence of interest is capable of controlling the transcription of the nucleotide sequence of interest into mRNA. A promoter is typically, though not necessarily, located 5' (i.e., upstream) of a nucleotide sequence of interest (e.g., proximal to the transcriptional start site of a structural gene) whose transcription into mRNA it controls, and provides a site for specific binding by RNA polymerase and other transcription factors for initiation of transcription.

Suitable promoters can be derived from genes of the host cells where expression should occur or from pathogens for this host cells (e.g., tissue promoters or pathogens like viruses). If a promoter is an inducible promoter, then the rate of transcription increases in response to an inducing agent. In contrast, the rate of transcription is not regulated by an inducing agent if the promoter is a constitutive promoter. Also, the promoter may be regulated in a tissue-specific or tissue preferred manner such that it is only active in transcribing the associated coding region in a specific tissue type(s) such as leaves, roots or meristem. The term "tissue specific" as it applies to a promoter refers to a promoter that is capable of directing selective expression of a nucleotide sequence or gene of interest to a specific type of tissue in the relative absence of expression of the same nucleotide sequence or gene of interest in a different type of tissue.

Although the foregoing invention has been described in some detail by way of illustration and example for purposes of clarity of understanding, certain changes and modifications may be practiced within the scope of the appended claims.

All publications and patent applications mentioned in the specification are indicative of the level of those skilled in the art to which this invention pertains. All publications and patent applications are herein incorporated by reference to the same extent as if each individual publication or patent application was specifically and individually indicated to be incorporated by reference.

The ability to make platelets in culture would be a valuable clinical and research tool. In order for in vitro production systems to be effective, however, they should be built to accommodate a high production capacity. Platelets are generated and consumed by the body very rapidly. It is estimated that ~$10^{11}$ new platelets are made every day, and that each platelet has a functional life span of only 7-10 days. For these reasons, successful transfusions typically require ~$1.5 \times 10^{11}$ platelets. Functional platelets can be derived from hematopoietic stem cells (HSCs). One of the hurdles to this approach, however, is that HSCs are difficult to grow and control in vitro, limiting the capacity to proliferate large numbers of patient-specific HSCs for that individual's specific therapeutic treatment. Furthermore, without an established infrastructure for long-term and reliable HSC expansion, it has been difficult to study the underlying mechanisms of HSC cell fate decisions. Thus, while the HSC lineage has been well characterized, the molecular mechanisms underlying cell fate decisions and differentiation remain unclear. This is particularly evident for the differentiation of the platelet progenitor cells called megakaryocytes (MK), and the subsequent production of platelets from MKs.

As an alternative, several groups have initiated in vitro systems by deriving MKs from embryonic stem (ES) cells or induced pluripotent stem (iPS) cells with the goal of producing a continuous supply of platelets for transfusion. Unfortunately, to date the production capacity of platelets from MKs derived from ES or iPS cells is insufficient, as published studies show significantly lower yields of ~20-400 platelets per MK than the ~$10^4$ platelets that are produced from a single MK cell in the bone marrow. This demonstrates that current cell culture approaches insufficiently replicate the endogenous bone marrow environment and/or that HSCs are an essential intermediate during the differentiation of healthy MKs. In comparison to ES and iPS cells, HSCs are the most studied and best characterized stem cell population.

Both extrinsic (environmental) mechanisms as well as intrinsic (transcription factor expression) mechanisms are thought to be involved in the regulation of HSC self-renewal and their commitment to differentiate into more specialized cell types. This interplay between extrinsic and intrinsic cues in hematopoiesis makes it difficult to replicate the HSC environment in vitro for enhancing their proliferation. Nonetheless, engineering a cell culturing system that better mimics the endogenous bone marrow niche is necessary for the production of high levels of platelets to support current therapeutic applications, and will likely facilitate the advance of future platelet-based therapies. Disclosed herein are methods using synthetic biology to replicate the dynamic extrinsic and intrinsic mechanisms that regulate HSC self-renewal and differentiation.

In addition to providing a replenishable supply of platelets for transfusion replacement, engineered platelets also have potential for additional therapeutic applications. Platelets circulate throughout the body and actively secrete proteins despite being anucleated. Disclosed herein are methods to engineer platelets to secrete biomolecules. For example, engineered platelets that secrete enzymes to breakdown plaque buildup in coronary arteries hold promise as a novel and noninvasive way to treat heart disease. Alternatively, engineered platelets can be used as diagnostic indicators if they are designed to secrete reporters that can be detected in the urine, for example, in response to metabolic or vascular disease. Moreover, engineered platelets can also be used to deliver cytokines or angiostatins to sites of cancerous growth. Disclosed herein are methods that can be used to generate a toolbox for genetically engineering HSC derivatives for a range of therapeutic applications.

Figures 2A, 2B:
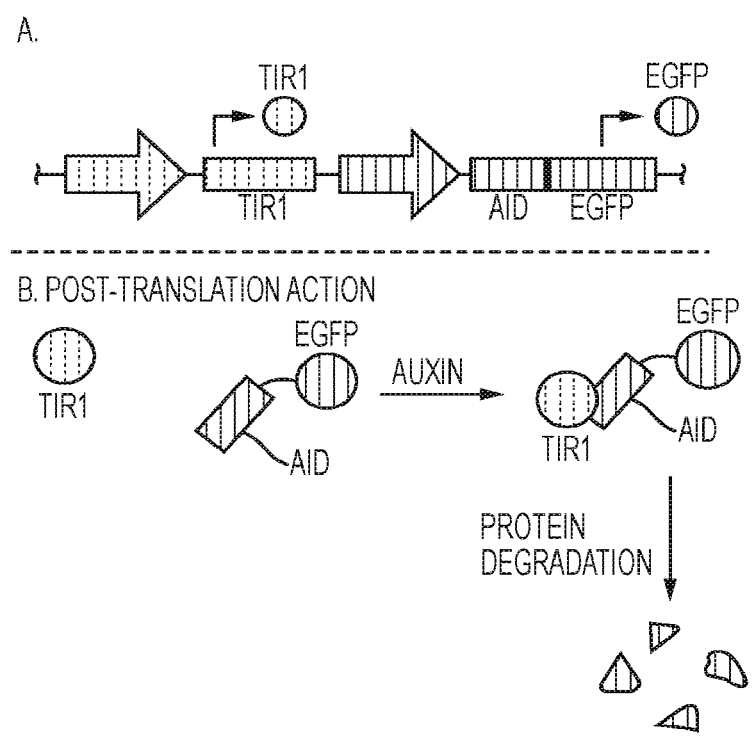
FIGS. 2A-B shows the auxin induced degron (AID) system.

Synthetic biology as a therapeutic research tool: The emerging field of synthetic biology has produced toolbox of genetic regulatory systems that can be applied in basic research and for therapeutic applications. Synthetic biology strategies can create opportunities to change basic research approaches and improve therapeutic treatments for treating injuries and diseases. The complexity of cell signaling networks can be simplified by considering genetic networks composed of subsets of simpler parts, or modules. This simplification is the foundation of synthetic biology, where engineering paradigms are applied in rational and systematic ways to produce predictable and robust systems for understanding or controlling cellular function. This approach entails reprogramming cells to perform in predictable ways. Towards this end, genetic circuits have been built out of DNA and RNA that enable cells to perform Boolean logic functions ranging from memory, and mathematical computations to higher-order cellular functions like cancer cell identification, controlling T cell populations, and reporting on the microenvironment. The engineered gene circuits underlying these functions include genetic switches, oscillators, digital logic gates, and cell counters and have been designed to regulate gene expression in dynamic and predictable ways. While the majority of work in synthetic biology has been in simple organisms such as yeast and bacteria, however, the therapeutic potential of cells carrying engineered genetic circuits has spurred interest in using synthetic biology to remediate or control human disease. This is in part based upon the premise that effective cell therapies require precise temporal and spatial regulation of gene expression, which can be easily controlled by using genetic circuits. Described herein are methods using synthetic biology tools to mimic and regulate the natural extrinsic and intrinsic mechanisms regulating HSC proliferation and differentiation into MKs for enhanced platelet production in an in vitro setting. Described herein are methods and compositions that can be applied independently and in combination:

i) LTRi: LTRi was one of the first mammalian genetic circuits capable of tight gene control that behaves like a rheostat and enables tightly regulated and graded levels of gene expression in response to the chemical inducer, isopropyl β-D-1-thiogalactopyranoside (IPTG). Thus much like a rheostat, gene expression is silent in the off state. In addition, LTRi is modular, allowing any mammalian transgene to be controlled in in vitro and in vivo model systems.

ii) Q-system: The Q system is a binary expression system developed in *Drosophila* that utilizes genes from *Neurospora crassa*. In the Q system, QF acts as a transcriptional activator that binds to the QUAS upstream regulatory sequence to drive reporter gene expression. This activation can be repressed by the QS protein, which blocks the QF transcriptional activation effects (FIG. 1). Gene expression can be activated using quinic acid (QA) which blocks QS repression of QF, thereby allowing for transcription of the reporter gene (FIG. 1D). The functionality of the Q system has been demonstrated in *Drosophila, Caenorhabditis elegans* (*C. elegans*) and in zebrafish. As disclosed herein, the Q system can be modified to enhance its functionality in mammalian cells (FIG. 1).

iii) Auxin: Plants have evolved a system in which a hormone, called auxin, induces rapid degradation of the AID-motif containing proteins. Moreover, auxin-mediated degradation of AID-tagged proteins has been shown to function in other eukaryotes, including mammalian cells. Thus, the auxin system can serve as a tool to control protein stability. Because other eukaryotes lack the auxin hormone, it can be used to conditionally control protein stability that enables rapid and reversible degradation of AID-tagged proteins in response to auxin (FIG. 2). As disclosed herein, this tool can be used in the construction of the genetic circuits described herein.

Approaches for incorporating genetic circuits into cells. Because many cells (e.g., HSCs) are difficult to grow and genetically manipulate in vitro, the modular technology disclosed herein can use CRISPR technology to insert a 'landing pad' for genetic circuits. Effectively applying synthetic biology requires that the array of genetic circuits and tools can be rapidly and efficiently introduced into the host cell genomes. Conventional techniques involve the random insertion of the genetic circuit into the genome, selecting stable clones in which the circuit is stably integrated into the genome, and testing the functionality of the circuit at that particular insertion site. These steps can be tedious and time consuming. Moreover, the testing phase is significant because each clone may be different and positional effects (e.g. due to local enhancers, repressors, or epigenetic modifications) may lead to the deregulation or misregulation of the circuit. To bypass these limitations, mouse embryonic stem (ES) cells can be engineered with 'docking sites' in the Rosa26 locus to allow for targeted and robust insertion of genetic circuits. The Rosa26 locus is used for achieving robust gene expression in mouse models and is resistant to epigenetic silencing. Using CRISPR/Cas9 technology, three attP sites can be added to the Rosa26 locus (FIG. 5A), which can allow unidirectional recombination at these sites to insert genetic circuits specifically at this locale (FIG. 5B). This allows a robust methodology for inserting any genetic circuit into the genome of mouse ES cells. Furthermore, because ES cells are totipotent, these genetically modified cells can be differentiated into a range of different functional cell types based upon the disease or tissue of interest. For the purpose of platelet production, genetically altered ES cells can initially be differentiated into HSCs. Another advantage of the ES cell approach is that the engineered cells can be rapidly expanded and maintained longer than alternatives such as primary HSCs, which rapidly reach senescence and spontaneously differentiate and therefore have a shorter functional lifetime. Furthermore, developing this technology allows for any genetic background of cell type to be used and ensures immune compatibility with the various mouse models.

Finally, the use of CRISPR technology can allow similar docking sites to be built in human cell lines.

Figure 4:
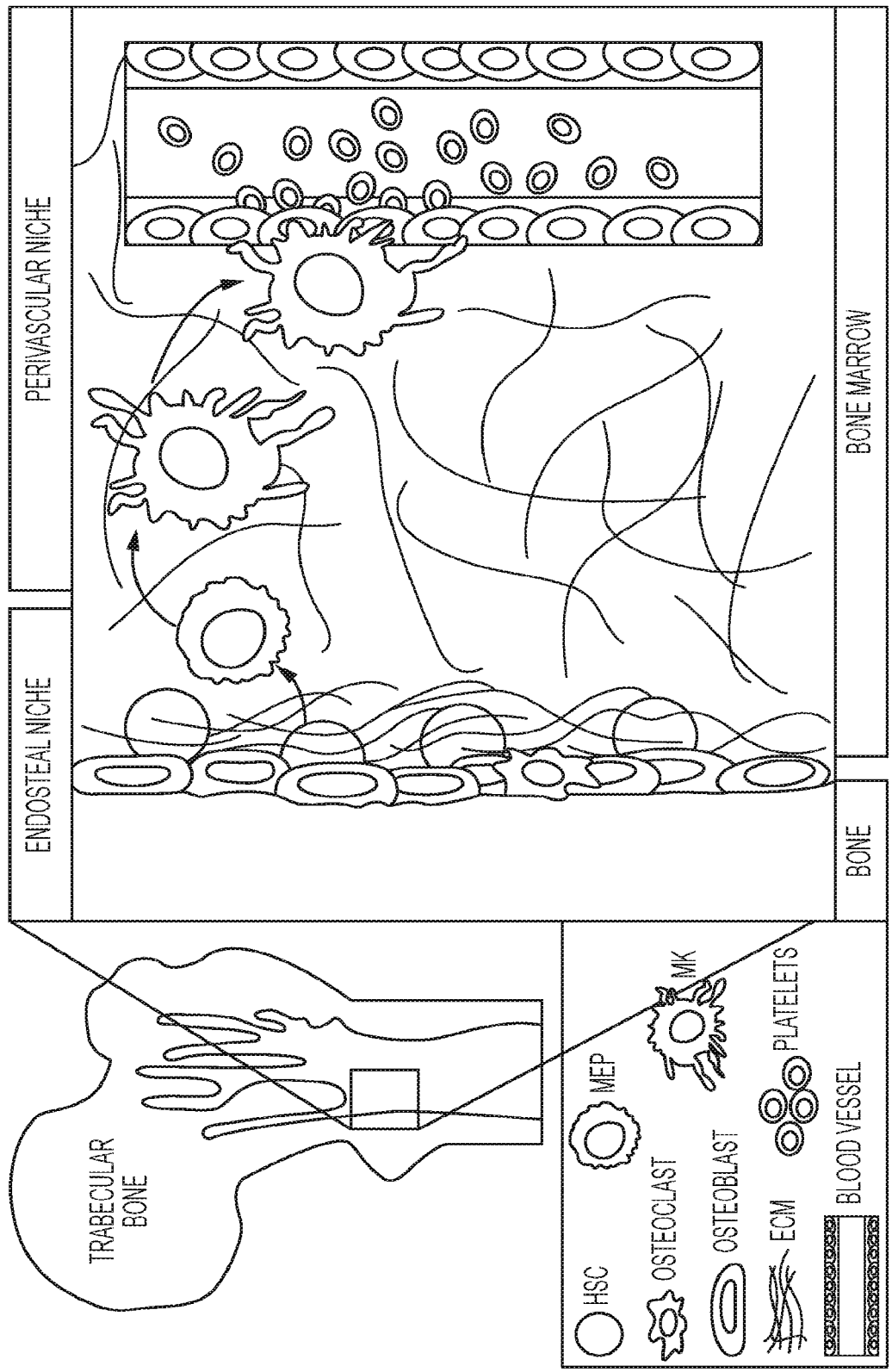
FIG. 4 shows the microenvironment of bone marrow in which hematopoietic stem cells (HSCs) remain in their multipotent state in the endosteal niche and become lineage-committed cells as they move to the perivascular niche.

A novel microenvironment for controlling the extrinsic and intrinsic cues for enhanced platelet production. Described herein are methods of producing cell-derived products that lack a nucleus. Also described herein is a cell culturing system that incorporates synthetic biology to better mimic the dynamic gene control in the bone marrow microenvironment (FIG. 4). HSCs are the most studied and best characterized stem cells. They are found in distinct spatial locations within the bone marrow, depending on their lineage specification and phenotype. Both extrinsic (environmental), as well as intrinsic (transcription factor expression) mechanisms are thought to be involved in the regulation of HSC self-renewal and proliferation; and their commitment to differentiate into more specialized cell types. This interplay between extrinsic and intrinsic cues in hematopoiesis has made it difficult control the HSC environment for enhancing their proliferation and directing differentiation. For example, significant progress has been made in identifying individual genes that are responsible for contributing to HSC proliferation (HoxB4/EPO), their differentiation into MEPs (EPO/TPO), their differentiation into MKs (Gata-1/TPO), and their terminal differentiation into platelets (TPO). It has yet to be determined, however, how these genes dynamically interact with each other throughout the life of HSCs.

Described herein is an engineered extrinsic microenvironment, wherein genetic circuits within the OP9 stromal cell layer can control the secretion of extrinsic factors in response to the addition of chemical inducers to the media. This can provide the correct combination of extrinsic cues in vitro to control the differentiation of HSCs to MKs for the production of platelets.

Mechanisms and compositions for incorporation into the disclosed genetic circuits can include one or more of the strategies disclosed in Cell 130, pp. 363-372, Jul. 27, 2007. The Cell, 2007 is hereby incorporated by reference for its teachings and disclosures of mechanisms and compositions for incorporation into genetic circuits.

Described herein is an engineered intrinsic microenvironment, using the attP docking system to insert genetic circuits into ES cells to control transcription factors in response to chemical inducers applied via the media. In this microenvironment, the level of various transcription factors can be controlled to differentiate ES cells into HSC-enriched populations, and then guide their differentiation to MKs for the production of platelets.

Figure 5:
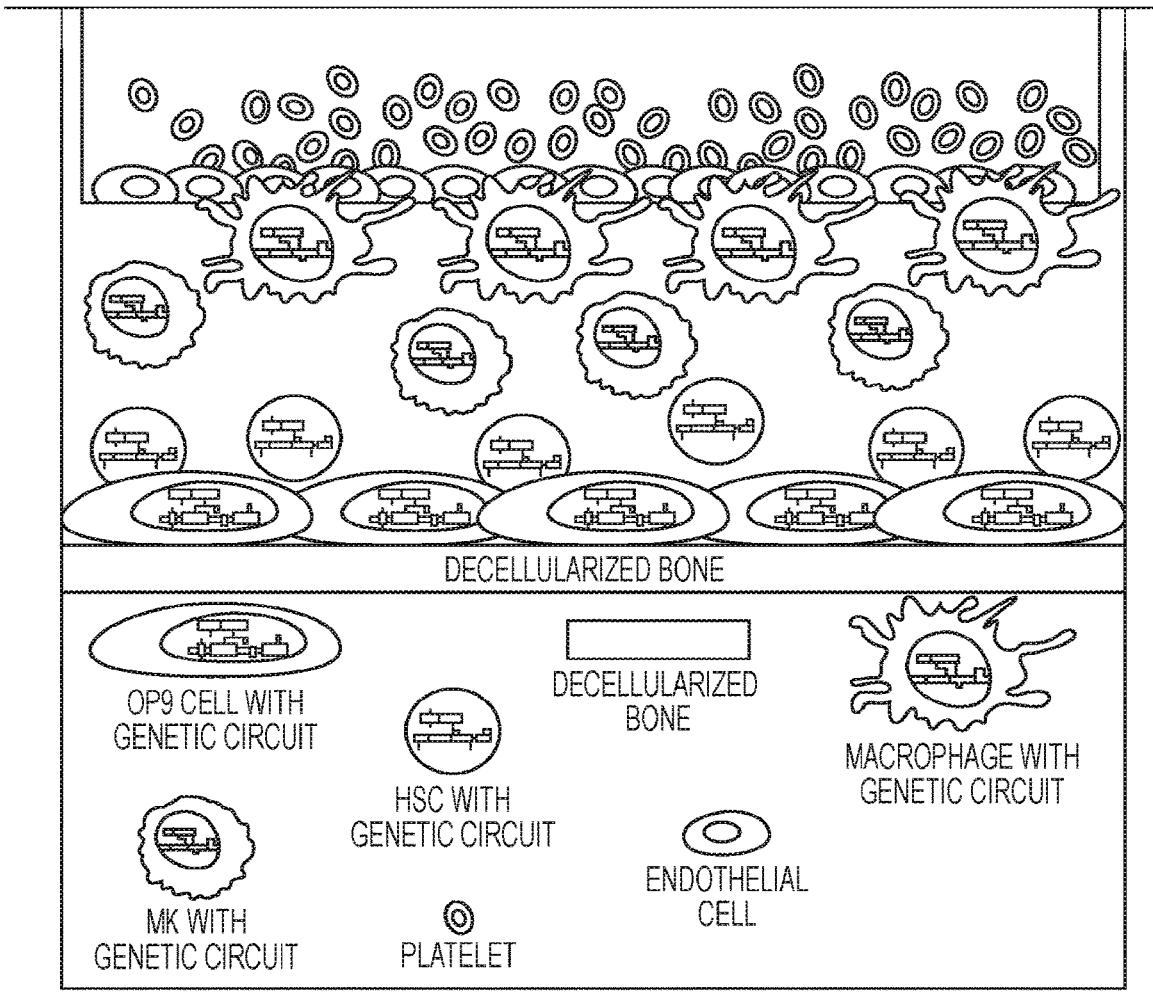
FIG. 5 is an overview of an engineered microenvironment showing a cell culture system that uses synthetic biology to mimic and control the extrinsic and intrinsic cues to enhance hematopoietic stem cell proliferation and differentiation for increased platelet production.

As described herein, the extrinsic and intrinsic environments can be built and characterized separately, and both can enhance HSC production when applied independently and can have a synergistic effect when they are applied together (FIG. 5). Moreover, engineered environment described herein can be used to improve in vitro proliferation of HSCs, in addition to studying the regulatory elements implicated in the commitment of MKs to platelets. Altogether, this system can create more functional platelets for infusion purposes.

Engineering platelets as delivery vehicles for therapeutic biomolecules. Platelets possess many characteristics that make them attractive candidates for in vivo delivery of natural and synthetic payloads: 1) they have extensive circulation range in the body, 2) they are anucleated cells, 3) they are biocompatible, 4) their average lifespan in humans is ~10 days, and 5) following activation, their protein granules serve as secretory vesicles, releasing components to the extracellular fluid. Using synthetic biology, MKs can be engineered to package therapeutic levels of protein cargo to be targeted for platelet secretion. The synthetic biology strategies described herein can be used to insert any genetic circuit into the genome of ES cells and differentiate them into a desired committed cell harboring that genetic circuit. This allows the flexibility to put in any therapeutic biomolecule to be expressed in differentiated cells.

To probe neurological disorders for improving diagnosis and treatment of neurodegenerative diseases. Disclosed herein are methods of treating neurodegenerative diseases. Neurodegeneration is a slow and progressive loss of neurons and axons in the central nervous system (CNS) that leads to neuronal dysfunction, as seen in acute and chronic neurodegenerative conditions such as Alzheimer's and Parkinson's diseases, neurotropic viral infections, stroke, traumatic brain injury, and multiple sclerosis. While the triggers of neurodegeneration vary, a common feature is chronic immune activation in the CNS. Approaches in synthetic biology as disclosed herein can be used to reprogram cells with genetic circuits to probe the CNS during the onset and progression of neurodegenerative diseases. Such an approach will enable a better understanding of the interactions between neuroinflammation and neurodegeneration that will have a major impact on the broad range of neurological disorders.

The healthy human body produces approximately $1 \times 10^{11}$ platelets each day. The source of this enormous cell population is from megakaryocytes (MKs), the precursor cells of platelets. The formation of MKs takes place in the bone marrow and involves the proliferation, maturation, and terminal differentiation of hematopoietic stem cells (HSCs).

Figure 6:
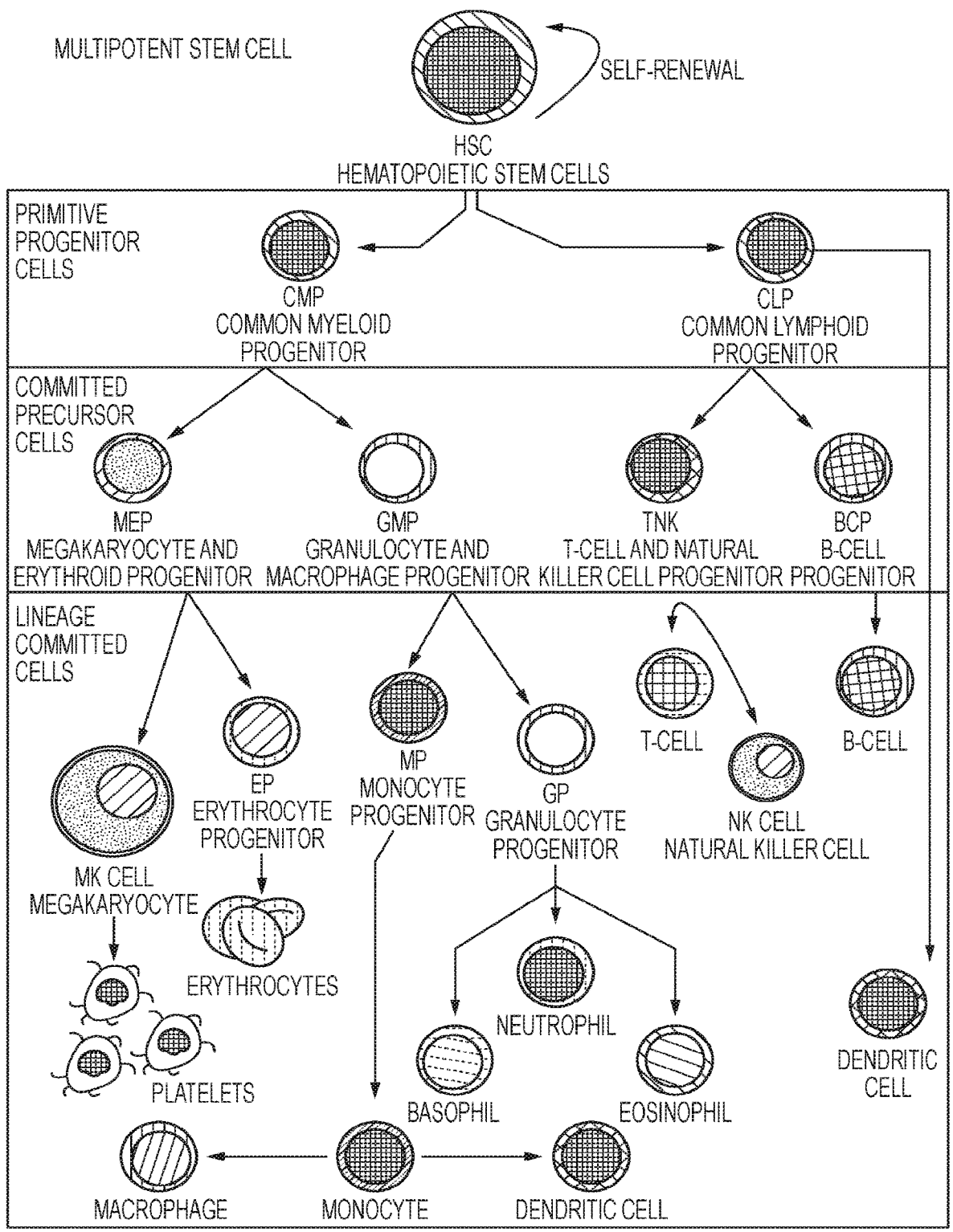
FIG. 6 is an overview of hematopoietic stem cell (HSC) differentiation showing that HSCs are multipotent stem cells that have the potential to differentiate into various precursor cells that become more specialized lineage specific cells.

HSCs are adult stem cells that have the potential to self-renew and differentiate into specialized blood and immune cells, which can be isolated from mobilized blood, umbilical cord blood, or bone marrow. HSCs are a potential source for platelet production; however, their numbers from isolations are generally so low that it restricts the full application of HSC transplantation. Furthermore, despite their ability to self-renew, it is surprisingly difficult to grow HSCs in culture, severely limiting their application potential. It is believed that this difficulty arises from the fact that HSCs require a complex microenvironment to keep them in a dynamic balance between self-renewal and differentiation. This complex environment includes the coordinated interplay between the interactions of extrinsic and intrinsic cues that contribute to HSC proliferation and their differentiation into lineage-committed cells (FIG. 6).

Figure 7:
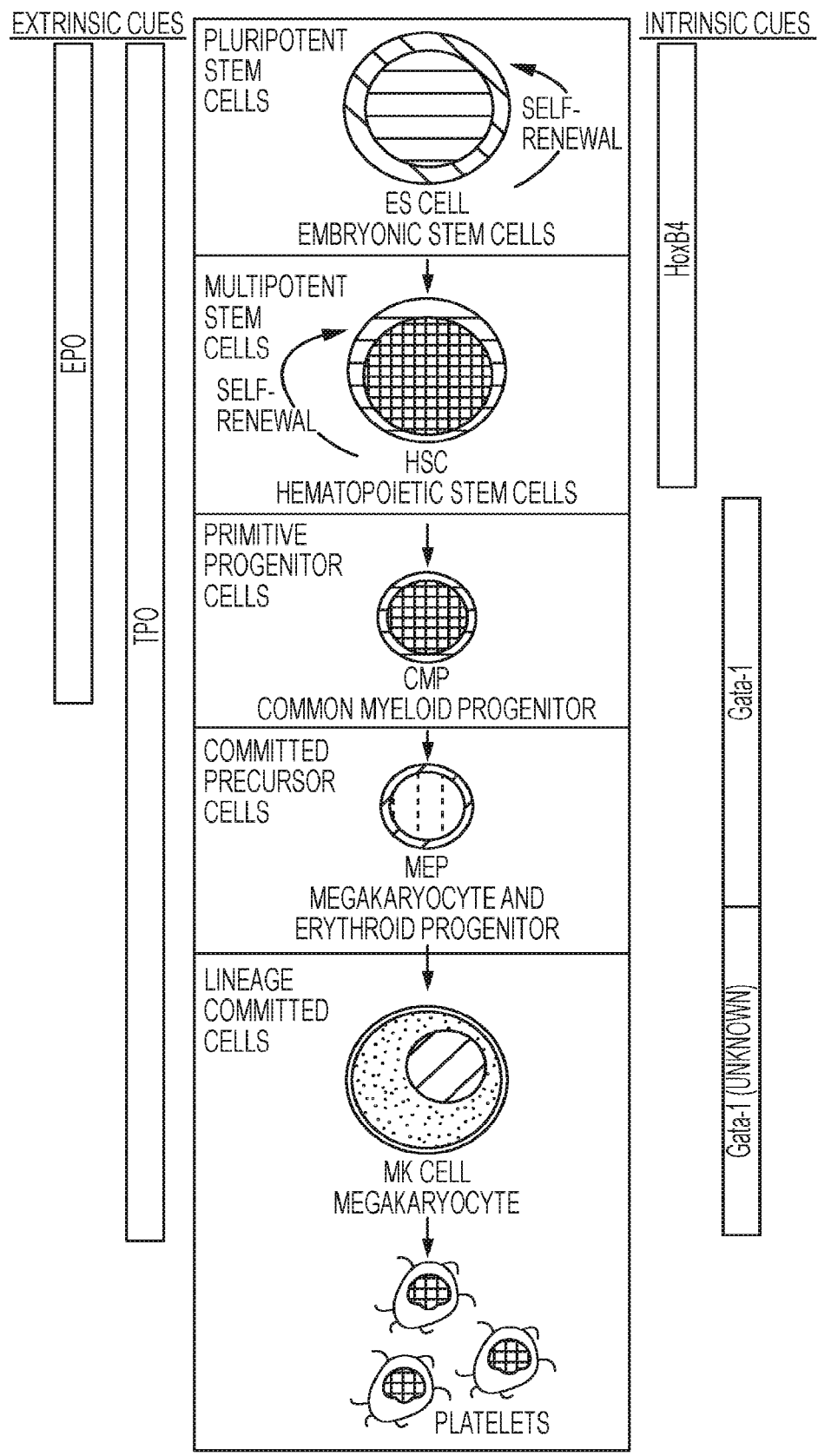
FIG. 7 shows the extrinsic and intrinsic signals responsible for the directed differentiation of embryonic stem (ES) cells to platelets.

Individual genes that contribute to the secreted extrinsic cues are EPO and TPO, while the intrinsic cues are the transcription factors HoxB4 and GATA-1 (FIG. 7). However, while the function of these factors have been implicated in vivo, parameters including dosage and timing that would be influenced effectively in vitro have not been established. Therefore, utilizing synthetic biology tools as described herein that enable the fine-tuning of gene expression can enhance the ability to replicate these dynamic events. Furthermore, there are many examples of gene expression in vivo that are highly dynamic during stem cell differentiation and development. A benefit to using tools in synthetic biology is that these complex patterns can be reproduced in vitro.

Described herein is a microenvironment engineered to better mimic the natural bone marrow and can allow enhanced proliferation of HSCs that can then enable a therapeutic relevant number of platelets to be produced. Disclosed herein are two complimentary approaches for controlling platelet production that could lead to the enhanced production and accelerated use of platelets as therapeutics. The first is based upon the observation that extrinsic cues play an important role in the differentiation of HSCs into megakaryocytes and platelets. This argues that HSCs receive signals from neighboring cells within their microenvironment to either maintain self-renewal or to differentiate into more specialized cells. The second is based upon the observation that intrinsic gene expression plays an important role in the differentiation of HSCs into megakaryocytes and platelets. This argues that HSCs control their own gene expression to self-renew or to differentiate into more specialized cells. Much work supports both of these hypotheses, and it is likely that HSC cell fate decisions are a combination of both extrinsic and intrinsic cues. The continuous generation of platelets from HSCs requires a highly complex series of molecular events. To this end, and disclosed herein are dynamic microenvironments engineered to control the contribution of extrinsic and intrinsic cues on HSC proliferation and differentiation of platelets, in addition to coupling these cues as one bio-inspired microenvironment.

Also disclosed herein, is the use these platelets as delivery vehicles for secreted therapeutic proteins. In addition to replacing missing cells, the in vitro production of non-nucleated cells from MKs in vitro can be used as a new therapeutic approach. These cells circulate throughout the body and can be engineered to have a systemic function, or can be used to identify sites of injury. Using synthetic biology, these cells can be engineered to detect changes in the body's homeostasis, whether it be an injury or blood glucose levels, to become activated and secrete factors therapeutic biomolecules. Alternatively, they could be used as biosensors, secreting an 'alarm factor' when the precursors for heart attacks are increased.

Each of these applications represents avenues through which synthetic biology can be applied in the treatment of human disease through HSCs and non-nucleated cells of the circulatory system. While the methodologies of building a cell culturing system capable of controlling HSC differentiation for platelet production, in addition to engineering platelets to secrete biomolecules, are presented in a linear path, the strength of this disclosure is that each of the approached described herein can improve the current state of producing platelets in vitro for therapeutic applications.

Based upon the need for improved tools to enhance the production of platelets for translation to the clinic, described herein are engineered microenvironments that: (1) control the contribution of extrinsic cues on HSC proliferation and differentiation of platelets, (2) control the intrinsic cues on HSC proliferation and differentiation of platelets, and (3) engineer platelets as delivery vehicles for biomolecules.

Methods

Disclosed herein are methods of producing red blood cells and platelets. The method can comprise the following steps. The method can include step a): providing a genetically engineered feeder cell. The feeder cell can include one or more genetic circuits. The one or more genetic circuits can include one or more genes of interest; and one or more promoters. The method can include step b): providing a genetically engineered fed cell. The fed cell can include one or more genetic circuits. The one or more genetic circuits can include one or more genes of interest; and one or more promoters. The one or more genes of interest can be different than the one or more genes of interest in a). The method can further include step c): culturing the genetically engineered feeder cell in a) with the genetically engineered fed cell in b). The culturing step can take place in a media under conditions that permit the genetically engineered fed cells to differentiate into red blood cells or platelets. The one or more of the genetically engineered fed cells as disclose herein can differentiate into red blood cells or platelets.

In an aspect, the one or more genetic circuits in method step a) and disclosed herein can be regulatable. In an aspect, the one or more genetic circuits can be regulated by one or more genes of interest of the genetic circuit in the genetically engineered fed cell. In an aspect, the one or more genetic circuits as disclosed herein can be regulated by the one or more genes of interest of the genetic circuit in the genetically engineered feeder cell.

In an aspect, the one or more genetic circuits as disclosed herein an in step a) can be regulated by one or more promoters. In an aspect, the one or more genetic circuits in step a) can further include one or more recombinases. In an aspect, the one or more recombinases can be, for example Cre or phiC31 integrase. In an aspect, the one or more recombinases can be regulatable. In an aspect, the one or more genetic circuits as disclosed herein and in a) can further include one or more recombination sites. In an aspect, the one or more recombination sites can be loxP, attP or Bxb1. In an aspect, the attP sites can be inserted at Rosa26 locus and/or in chromosome 11.

As used herein, the term "promoter" refers to regulatory elements, promoters, promoter enhancers, internal ribosomal entry sites (IRES) and other elements that are capable of controlling expression (e.g., transcription termination signals, including but not limited to polyadenylation signals and poly-U sequences). Promoters can direct constitutive expression. Promoters can also direct expression in a temporal-dependent manner including but not limited to cell-cycle dependent or developmental stage-dependent. Examples of promoters include but are not limited to WPRE, CMV enhancers, and SV40 enhancers. Specific gene specific promoters can be used. Such promoters allow cell specific expression or expression tied to specific pathways. Any promoter that is active in mammalian cells can be used. In an aspect, the promoter is an inducible promoter including, but not limited to, Tet-on and Tet-off systems. Such inducible promoters can be used to control the timing of the desired expression. In an aspect, the promoter can be an inducible promoter. Examples of inducible promoters include but are not limited to tetracycline inducible system (tet); heat shock promoters and IPTG activated promoters. In some aspects, promoters are bidirectional.

The promoter and/or enhancer can be specifically activated either by light or specific chemical events which trigger their function. Systems can be regulated by reagents such as tetracycline and dexamethasone.

In some aspects, the genetic circuits as disclosed herein can comprise a promoter, for example but not limited to, enhancers, 5' untranslated regions (5'UTR), 3' untranslated regions (3'UTR), and repressor sequences; constitutive promoters, inducible promoter; tissue specific promoter, cell-specific promoter or variants thereof. Examples of tissue-specific promoters include, but are not limited to, albumin, lymphoid specific promoters, T-cell promoters, neurofilament promoter, pancreas specific promoters, milk whey promoter; hox promoters, a-fetoprotein promoter, human LIMK2 gene promoters, FAB promoter, insulin gene promoter, transphyretin, alpha.1-antitrypsin, plasminogen activator inhibitor type 1 (PAI-1), apolipoprotein myelin basic protein (MBP) gene, GFAP promoter, OPSIN promoter, NSE, Her2, erb2, and fragments and derivatives thereof. Examples of other promoters include, but are not limited to, tetracycline, metallothionine, ecdysone, mammalian viruses (e.g., the adenovirus late promoter; and the mouse mammary tumor virus long terminal repeat (MMTV-LTR)) and other steroid-responsive promoters, rapamycin responsive promoters and variants thereof.

The one or more genetic circuits disclosed herein and in step a) can further include one or more repressor proteins. In an aspect, the one or more repressor proteins can be LacI, TetR, and/or QS. In an aspect, the one or more repressor proteins disclosed herein can be regulatable.

The media can further include one or more modulators. In an aspect, the one or more modulators can modulate (e.g., repress or activate) the genetic circuits of a) or b) as disclosed herein. In an aspect, the one or more genetic circuits disclosed herein an in step a) can be regulated by one or more media modulators. In an aspect, the one or more media modulators can be isopropyl β-D-1-thiogalactopyranoside (IPTG), tetracycline, doxycycline, quinic acid, or auxin.

The method disclosed herein can also include one or more genetic circuits in step a) that are non-regulatable. In an aspect, the one or more promoters of the genetic circuits as disclosed herein and in step a) can be constitutively expressed. In an aspect, the one or more promoters of the genetic circuits disclosed herein and in step a) can be CMV, RSV and/or U6, beta actin, and/or elongation factor promoters. In an aspect, the one or more promoters can include one or more operator sites (e.g., tet). Such operator sites can allow for one or more repressor proteins to bind.

The method disclosed herein can also include one or more genes of interest of the genetic circuits in step a). In an aspect, the one or more genes of interest of the genetic circuits disclosed herein can be erythropoietin, thrombopoietin, and/or IL1-α. In an aspect, the one or more genes of interest of the genetic circuits disclosed herein and in step a) can be constitutively expressed.

The method disclosed herein can include a genetically engineered feeder cell. In an aspect, the genetically engineered feeder cell can be derived from an embryonic stem cell or a mouse embryonic stem cell. In an aspect, the genetically engineered feeder cell can be an osteoblast. In an aspect, the osteoblast can be an OP-9 stromal cell. In an aspect, the osteoblast can be from cord blood or bone marrow. In an aspect, the genetically engineered feeder cell can be derived from an immortalized cell line. In an aspect, the genetically engineered feeder cell can support undifferentiated hematopoietic stem cell (HSC) growth. In an aspect, the genetically engineered feeder cell is capable of being genetically engineered.

The methods disclosed herein can use a variety of cells. Examples of cells include but are not limited to stem cells, such as embryonic stem cells.

The method disclosed herein can include one or more genetic circuits as described herein and in b) that can be regulatable. In an aspect, the one or more genetic circuits in b) can be regulated by one or more genes of interest of the genetic circuit in the genetically engineered fed cell. In an aspect, the one or more genetic circuits in b) can be regulated by one or more genes of interest of the genetic circuit in the genetically engineered feeder cell. In an aspect, one or more genetic circuits in b) can further comprise one or more recombinases. In an aspect, one or more recombinases can be Cre or phiC31 integrase. In an aspect, one or more recombinases can be regulatable.

The method disclosed herein can include one or more genetic circuits as described herein and in step b) that further comprise one or more recombination sites. In an aspect, one or more recombination sites can be loxP, attP or Bxb1. In an aspect, the attP, loxP, or Bxb1 sites can be inserted at Rosa26 locus. In an aspect, the one or more genetic circuits disclosed herein and in step b) can be regulated by one or more promoters. In an aspect, one or more genetic circuits disclosed herein and in step b) can further comprise one or more repressor proteins. In an aspect, one or more repressor proteins can be LacI, TetR, or QS. In an aspect, one or more repressor proteins can be regulatable.

In an aspect, one or more genetic circuits disclosed herein and in step b) can be regulated by one or more media modulators. In an aspect, one or more modulators can be isopropyl β-D-1-thiogalactopyranoside (IPTG), tetracycline, doxacycline, quinic acid, or auxin. Such media modulators or agents are well known in the art.

The method disclosed herein can include one or more genetic circuits described herein and in step b) that can be non-regulatable. In an aspect, one or more promoters of the genetic circuits disclosed herein and in step b) can be constitutively active. In an aspect, one or more promoters of the genetic circuits in step b) can be CMV, RSV U6, beta actin, and/or elongation factor promoters. In an aspect, one or more promoters (e.g., CMV, RSV and/or U6) can comprise one or more operator sites. The operator sites can allow for repressor proteins to bind.

In an aspect, one or more genes of interest of the genetic circuits disclosed herein and in step b) can be HoxB4 and/or GATA-1. In an aspect, one or more genes of interest of the genetic circuits disclosed herein and in step b) can be constitutively expressed. In an aspect, GATA-1 comprises an auxin protein degradation tag.

The genetically engineered fed cells described herein can be hematopoietic progenitor stem cells. In an aspect, the hematopoietic stem cell can be derived from cord blood, bone marrow, iPS cell, or ES cell. In an aspect, the genetically engineered fed cell can be capable of producing progenitor cells of platelets and red blood cells. In an aspect, the progenitor cells can be capable of producing platelets and red blood cells. In an aspect, the progenitor cells can comprise one or more of the genetic circuits disclosed herein. In an aspect, the progenitor cells comprise one or more of the genetic circuits disclosed herein that can regulate the expression of any of the one or more genes of interest. In an aspect, one or more genes of interest can be HoxB4 and/or GATA-1. The genetic circuits described herein also can comprise one or more repressor proteins (e.g., LacI, TetR or QS) and can be controlled by one or more medial modulators (e.g., isopropyl β-D-1-thiogalactopyranoside (IPTG), tetracycline, doxacycline, quinic acid, or auxin).

The gene of interest can by any gene. It can be endogenous or introduced. The terms "target," "target gene," and "target nucleotide sequence" can be used interchangeably and refers to gene of interest. For example, a target gene is a gene of known function or is a gene whose function is unknown, but whose total or partial nucleotide sequence is known. Alternatively, the function of a target gene and its nucleotide sequence are both unknown. A target gene can be a native gene of the eukaryotic cell or can be a heterologous gene which has previously been introduced into the eukaryotic cell or a parent cell of said eukaryotic cell, for example by genetic transformation. A heterologous target gene can be stably integrated in the genome of the eukaryotic cell or is present in the eukaryotic cell as an extrachromosomal molecule, e.g., as an autonomously replicating extrachromosomal molecule. A target gene can include polynucleotides comprising a region that encodes a polypeptide or polynucleotide region that regulates replication, transcription, translation, or other process important in expression of the target protein; or a polynucleotide comprising a region that encodes the target polypeptide and a region that regulates expression of the target polypeptide; or non-coding regions such as the 5' or 3' UTR or introns. A target gene may refer to, for example, an mRNA molecule produced by transcription a gene of interest.

The design or construction of the genetic circuits disclosed herein can be carried out in a modular fashion, allowing for the regulation of any gene, including heterologous and other recombinant genes. In some aspects, the parts or modules can be genetic activators, genetic repressors, recombinases, genome editing, and synthetic transcription factors. In some aspects, the genetic circuit described herein can comprise one or more modules.

Vectors can be introduced in a prokaryote, amplified and then the amplified vector can be introduced into a eukaryotic cell. The vector can also be introduced in a prokaryote, amplified and serve as an intermediate vector to produce a vector that can be introduced into a eukaryotic cell (e.g., amplifying a plasmid as part of a viral vector packaging system). A prokaryote can be used to amplify copies of a vector and express one or more nucleic acids to provide a source of one or more proteins for delivery to a host cell or host organism. Expression of proteins in prokaryotes is often carried out in *Escherichia coli* with vectors containing constitutive or inducible promoters directing the expression of either fusion or non-fusion proteins. Vectors can also be a yeast expression vector (e.g., *Saccharomyces cerevisiae*).

In some aspects, the vector is capable of driving expression of one or more sequences in mammalian cells using a mammalian expression vector. Examples of mammalian expression vectors include but are not limited to pCDM8 and pMT2PC. In mammalian cells, regulatory elements control the expression of the vector. Examples of promoters are those derived from polyoma, adenovirus 2, cytomegalovirus, simian virus 40, and others disclosed herein and known in the art.

The method disclosed herein can include conditions in step c) that permit the expression of one or more genes of interest in steps a) or b). In an aspect, osteoblasts can be contacted, exposed to or treated with mitomycin-C. The osteoblasts can be washed before the stem cells are added. The osteoblasts can be washed to remove the mitomycin-C. Generally, the osteoblasts can be prepared accordingly to standard protocol that is known to one of ordinary skill in the art. The osteoblasts, for example, can be treated with mitomycin-C prior to or just before growing additional cells on top of the feeder cells.

In an aspect, the medium that can be used in the methods disclosed herein can comprise one or more components or modulators. The one or more components or modulators can lead to the formation of platelet and/or red blood cell progenitor stem cells. In an aspect, one or more components or modulators described herein can be isopropyl β-D-1-thiogalactopyranoside (IPTG), tetracycline, doxacycline, quinic acid, or auxin. In an aspect, the progenitor stem cells can produce platelet and/or red blood cell precursor cells. In an aspect, the progenitor stem cells can express one or more self-identifying cell surface markers. In an aspect, the progenitor stem cells can express GATA-1 and/or HoxB4. In an aspect, the expression of one or more cell surface markers can be produced by the genetic circuit disclosed herein. In an aspect, the one or more cell surface markers can be self-identifying. In an aspect, one or more cell surface markers can be CD13, CD34, CD41a, and CD43.

In an aspect, the platelets and/or red blood cells produced by the method described herein can express one or more cell surface markers. In an aspect, one or more cell surface markers can be CD41a and CD42b.

In an aspect, the method disclosed herein can further comprise step d): isolating and purifying the platelets or red blood cells.

Methods of Treating

Disclosed herein are methods of treating a patient. In an aspect, the patient can be in need of a platelet or red blood cell transfusion. The method can comprise administering a therapeutically effective amount the in vitro produced and isolated platelets or red blood cells. The in vitro produced and isolated platelets or red blood cells can be produced by any of the methods disclosed herein.

Disclosed herein are methods of producing platelets or red blood cells comprising a therapeutic agent. The method can comprise any of the methods disclosed herein to produce platelets and/or red blood cells harboring therapeutic proteins within them to be released in the body. The method can comprise extrinsic and/or intrinsic regulation as described herein.

Disclosed herein are methods of producing platelets or red blood cells comprising therapeutic agents. The method can comprise the steps: a) providing a genetically engineered feeder cell, wherein the feeder cell comprises one or more genetic circuits; wherein the one or more genetic circuits comprise one or more genes of interest; and one or more promoters; b) providing a genetically engineered fed cell, wherein the fed cell comprises one or more genetic circuits; wherein the one or more genetic circuits comprise one or more genes of interest, wherein the one or more genes of interest are different than the one or more genes of interest in a); and one or more promoters; c) culturing the genetically engineered feeder cell in a) with the genetically engineered fed cell in b) in a media under conditions that permit the genetically engineered fed cells to differentiate into platelet and/or red blood cell progenitor stem cells; and d) producing platelets or red blood cells comprising therapeutic agents. The progenitor stem cells are capable of producing the therapeutic agent. The progenitor stem cells can be regulated intrinsically or extrinsically to produce or secrete the therapeutic agent.

As used herein, the term "therapeutic agent" refers to a chemical compound, a protein, a peptide, a small molecule, an antibody or a cell.

Therapeutic proteins or agents as disclosed herein can be transcribed from genetic circuits in platelet and red blood cell progenitor stem cells, prior to the terminal differentiation into platelets or red blood cells. These therapeutic proteins or agents can be present in the cytoplasm of progenitor cells and, therefore, be a part of the terminally differentiated platelets and/or red blood cells. The production of therapeutic proteins or agents can be transcribed from constitutively expressing promoters, and/or with inducible genetic circuits.

In an aspect, the method disclosed herein can further comprise the step: e) re-culturing the progenitor stem cells produced step c) in a media under conditions promoting the differentiation of the progenitor stem cells into platelets and/or red blood cells. In an aspect, the method disclosed herein can further comprise the step: f) collecting and isolating the platelets and red blood cells.

The methods disclosed herein can be carried out to produce therapeutic cells. Therapeutic cells can comprise one or more therapeutic agents. In an aspect, the therapeutic agent can be a small molecule, a gene, a peptide, a vaccine, or an antimicrobial.

In an aspect, the one or more genetic circuits in a) are regulatable. In an aspect, the one or more genetic circuits in a) can be regulated by the one or more genes of interest of the genetic circuit in the genetically engineered fed cell. In an aspect, the one or more genetic circuits in a) can be regulated by the one or more genes of interest of the genetic circuit in the genetically engineered feeder cell.

In an aspect, the one or more genetic circuits in a) can be regulated by one or more promoters. In an aspect, the one or more promoters of the genetic circuit in a) and b) can be CMV, RSV and/or U6. In an aspect, the one or more promoters (e.g., CMV, RSV and/or U6) can comprise an operator site (e.g., tet).

In an aspect, the one or more genetic circuits in a) can further comprise one or more recombinases. In an aspect, the one or more recombinases can be Cre, phiC31 integrase and/or Bxb1. In an aspect, the one or more recombinases can be regulatable. In an aspect, the one or more genetic circuits in a) can further comprise one or more recombination sites. In an aspect, the one or more recombination sites can be loxP or attP. In an aspect, the attP or any other recombinase recognition sites can be inserted at Rosa26 and/or chromosome 11 locus. In an aspect, the attP and any other integrase recognition cites can serve as the insertion site for the therapeutic agent.

In an aspect, the one or more genetic circuits in a) can further comprise one or more repressor proteins. In an aspect, the one or more repressor proteins can be LacI, TetR, and/or QS. In an aspect, the one or more repressor proteins can be regulatable.

In an aspect, the media disclosed herein can further comprise one or more components or modulators. In an aspect, the one or more genetic circuits in a) and b) can be regulated by one or more media modulators or components. In an aspect, the one or more media modulators or components can be isopropyl β-D-1-thiogalactopyranoside (IPTG), tetracycline, doxycycline, quinic acid, or auxin.

In an aspect, the one or more genes of interest of the genetic circuit in a) can be thrombopoietin. In an aspect, thrombopoietin can be constitutively expressed.

In an aspect, the one or more genetic circuits in b) can be regulatable. In an aspect, the one or more genetic circuits in b) can be regulated by the one or more genes of interest of the genetic circuit in the genetically engineered fed cell. In an aspect, the one or more genetic circuits in b) can be regulated by the one or more genes of interest of the genetic circuit in the genetically engineered feeder cell.

In an aspect, the one or more genetic circuits in b) can be regulated by one or more promoters. In an aspect, the one or more promoters of the genetic circuit in b) can be CMV, RSV and/or U6.

In an aspect, the one or more genetic circuits in b) can further comprise one or more recombinases. In an aspect, the one or more recombinases can be phiC31 integrase or Cre. In an aspect, the one or more recombinases can be regulatable. In an aspect, the one or more genetic circuits in b) can further comprise one or more recombination sites. In an aspect, the one or more recombination sites can be loxP, attP or Bxb1. In an aspect, the attP, loxP or Bxb1 sites can be inserted at Rosa26 locus. In an aspect, the one or more recombination sites can serve as the insertion site for the therapeutic agent.

As described herein, the recombinase sites in the genome, for example, attP, can be used to insert any of the genetic circuits disclosed herein into the genome via a 'docking site.' This docking site allows for the targeted and robust insertion of the genetic circuits disclosed herein into the genome that are known to be robust in achieving gene expression and can be resistant to epigenetic silencing.

The location of the therapeutic agent can be in the genome.

In an aspect, the one or more genetic circuits in b) can further comprise one or more repressor proteins. In an aspect, the one or more repressor proteins can be LacI, TetR, and/or QS. In an aspect, one or more repressor proteins can be regulatable.

In an aspect, the media disclosed herein can further comprise one or more modulators. In an aspect, the one or more media modulators can be isopropyl β-D-1-thiogalactopyranoside (IPTG), tetracycline, doxycycline, quinic acid, or auxin.

In an aspect, the one or more genes of interest of the genetic circuit in b) can be GATA-1. In an aspect, GATA-1 can be constitutively expressed.

In an aspect, the platelet or red blood cell progenitor stem cells in step c) can express one or more cell surface markers. In an aspect, the platelet or red blood cell progenitor stem cells in step c) can express GATA-1. In an aspect, the one or more surface markers can be CD13, CD34, CD41a, and CD43. In an aspect, the platelets or red blood cells can express one or more cell surface markers. In an aspect, the one or more cell surface markers can be CD41a and CD42b.

Disclosed herein are methods of treating a patient in need of a therapeutic agent. The method can comprise administering a therapeutically effective amount of therapeutic platelets and/or red blood cells to the subject or patient. The method can comprise identifying a patient in need of treatment. The method can comprise administering to the patient a therapeutically effective amount of the isolated platelets and/or red blood cells. In an aspect, the platelets and/or red blood cells comprise a therapeutic agent. The isolated platelets and red blood cells do not contain DNA. These cells express the proteins and peptides that they were engineered to express via the methods disclosed herein. These cells are anucleated.

Therapeutic administration encompasses prophylactic applications. Based on genetic testing and other prognostic methods, a physician in consultation with their patient can choose a prophylactic administration where the patient has a clinically determined predisposition or increased susceptibility (in some cases, a greatly increased susceptibility) to a type of condition disorder or disease.

The platelets and red blood cells as well as the platelets and red blood cells comprising a therapeutic agent described herein can be administered to the subject (e.g., a human patient) in an amount sufficient to delay, reduce, or preferably prevent the onset of clinical disease. Accordingly, in some aspects, the patient is a human patient. In therapeutic applications, compositions are administered to a subject (e.g., a human patient) already with or diagnosed with a condition, disorder or disease in an amount sufficient to at least partially improve a sign or symptom or to inhibit the progression of (and preferably arrest) the symptoms of the condition, its complications, and consequences. An amount adequate to accomplish this is defined as a "therapeutically effective amount." A therapeutically effective amount of a platelets and red blood cells as well as the platelets and red blood cells comprising a therapeutic agent described herein can be an amount that achieves a cure, but that outcome is only one among several that can be achieved. One or more of the symptoms can be less severe. Recovery can be accelerated in an individual who has been treated.

The therapeutically effective amount of one or more of the therapeutic agents present within the platelets and red blood cells described herein and used in the methods as disclosed herein applied to mammals (e.g., humans) can be determined by one of ordinary skill in the art with consideration of individual differences in age, weight, and other general conditions (as mentioned above).

The platelets and red blood cells including platelets and red blood cells comprising a therapeutic agent described herein can be formulated for administration by any of a variety of routes of administration.

The platelets and red blood cells including platelets and red blood cells comprising a therapeutic agent can be prepared for parenteral administration. Platelets and red blood cells prepared for parenteral administration includes those prepared for intravenous (or intra-arterial), intramuscular, subcutaneous, and intraperitoneal, administration.

EXAMPLES

Example 1: Engineer a Microenvironment to Deliver Extrinsic Cues That Enhance Differentiation of Platelets The cellular environment, or niche, housing a population of stem cells, contains extrinsic factors that regulate the multipotent or differentiated state of hematopoietic stem cells. This is evident at the bench where it is common to grow HSCs on a layer of stromal support cells to maintain a supporting environment for HSCs to grow and differentiate. It is generally thought that the supporting cells produce many cytokines that maintain HSCs in their multipotent state, in addition to guiding their cell fate decisions. Individual cytokines can promote lineage specification, or they can regulate the proliferation and maintain stem cells in their multipotent state. Two cytokines, erythropoietin (EPO), and thrombopoietin (TPO) have been shown to be important mediators that support the lineage commitment of HSCs to the megakaryocyte/erythroid progenitor (MEP) and MK lineages (FIG. 7). Despite this demonstrated significance, however, the dosage and temporal dynamics of cytokine application in vitro has yet to be established.

For the production of platelets, EPO needs to be turned off (or down regulated) after the cells have reached the MEP stage of differentiation. Otherwise, continued exposure to high levels of EPO will drive the MEPs to become RBCs (FIG. 7). In contrast, TPO has been shown to have such a strong effect on platelet production. As a result, clinical trials evaluating the use of recombinant TPO and TPO mimetics to treat thrombocytopenia have taken place. Unfortunately, this has had limited success as some patients developed antibodies that caused a decrease in platelets, and/or the development of bone marrow myelofibrosis. Furthermore, many of these TPO molecules take 12 days to reach maximum effect, making them less useful in acute situations. Despite these caveats, the potential of TPO to act as a potent potentiator of platelet production in vitro remains high and as a result TPO will be elevated in conjunction with EPO as extrinsic factors promoting platelet production in the in vitro system described herein.

This co-cultured approach has the benefit that cytokine production and secretion occurs in close proximity to the target cells, thus limiting concerns about protein stability and diffusion while the genetic switches allow cytokine production to mimic patterns described in vivo.

Figure 8:
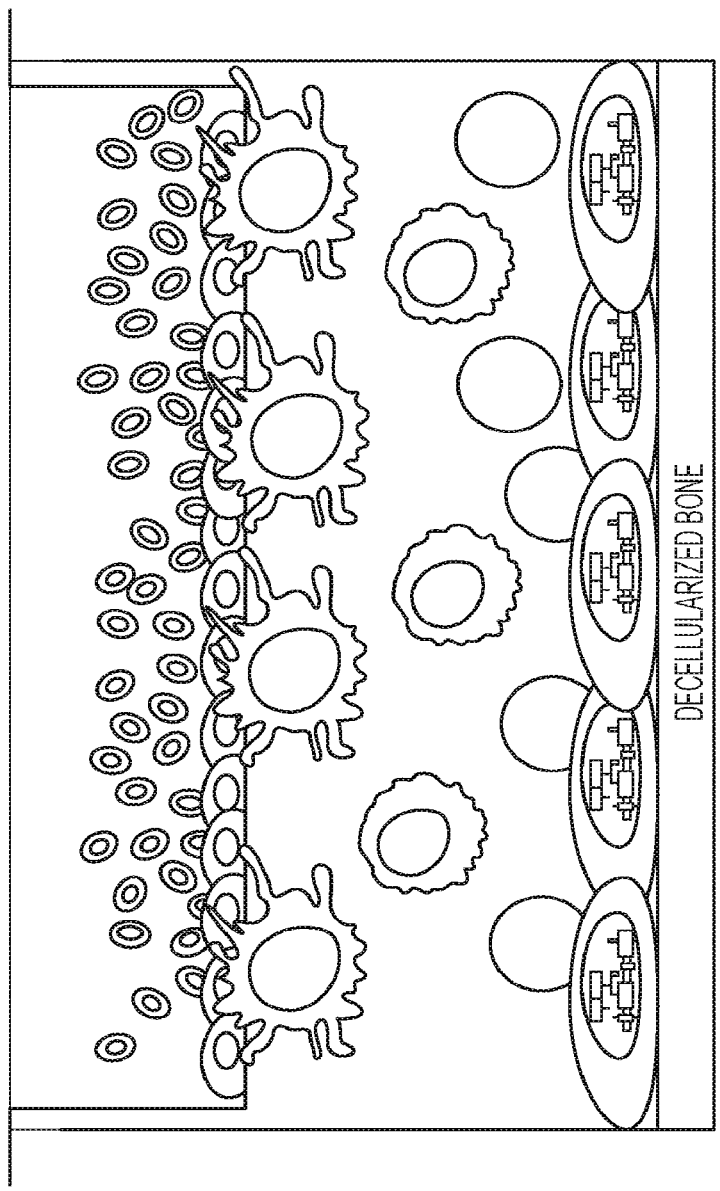
FIG. 8 depicts the engineered extrinsic environment showing decellularized mouse femurs can be used to grow OP9 cells with genetic circuits to enhance hematopoietic stem cell differentiation into platelets.
Figure 9:
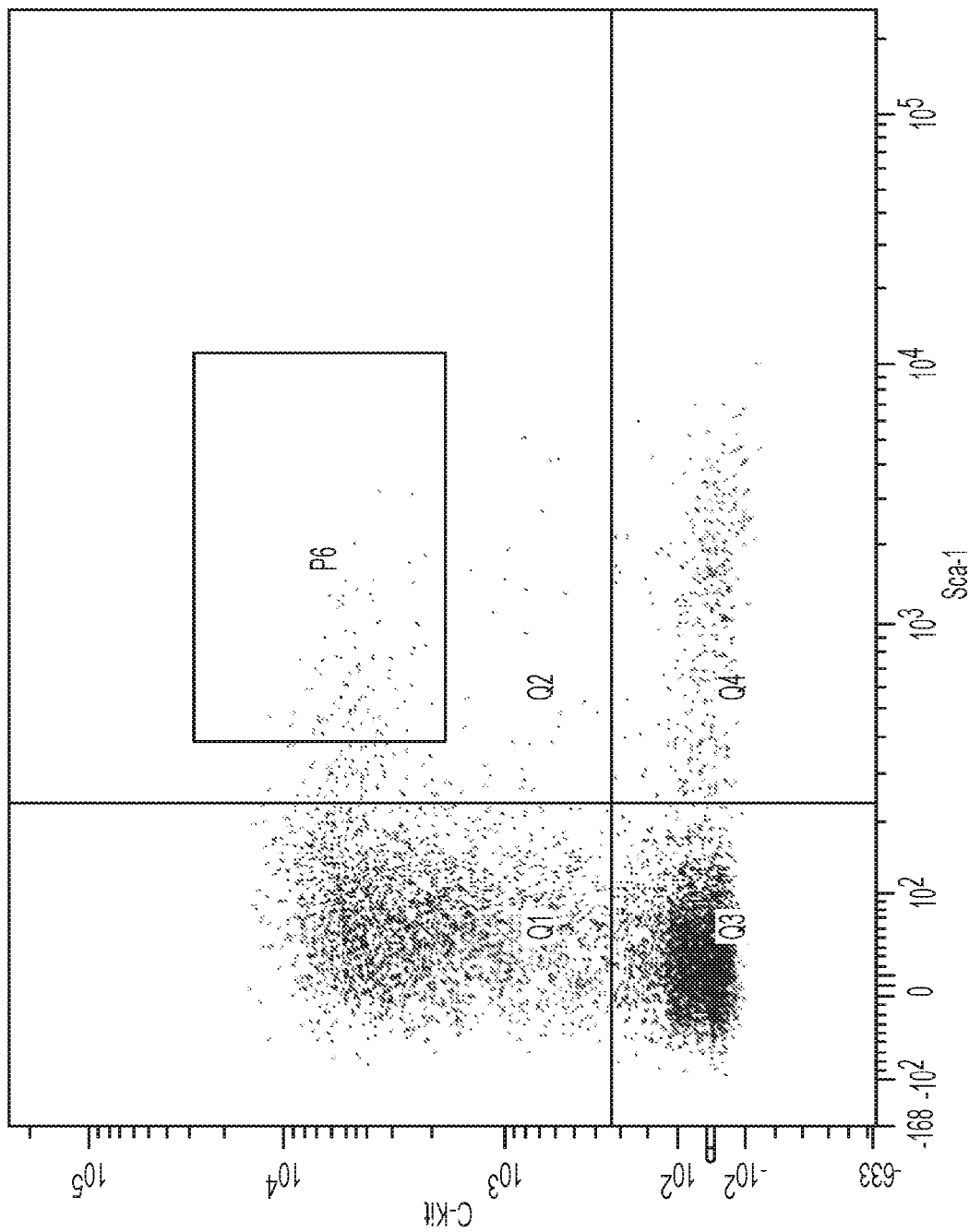
FIG. 9 shows LSK (Lin-Sca1+Kit-) cells that are sorted are in the P6 region.
Figures 10A, 10B, 10C:
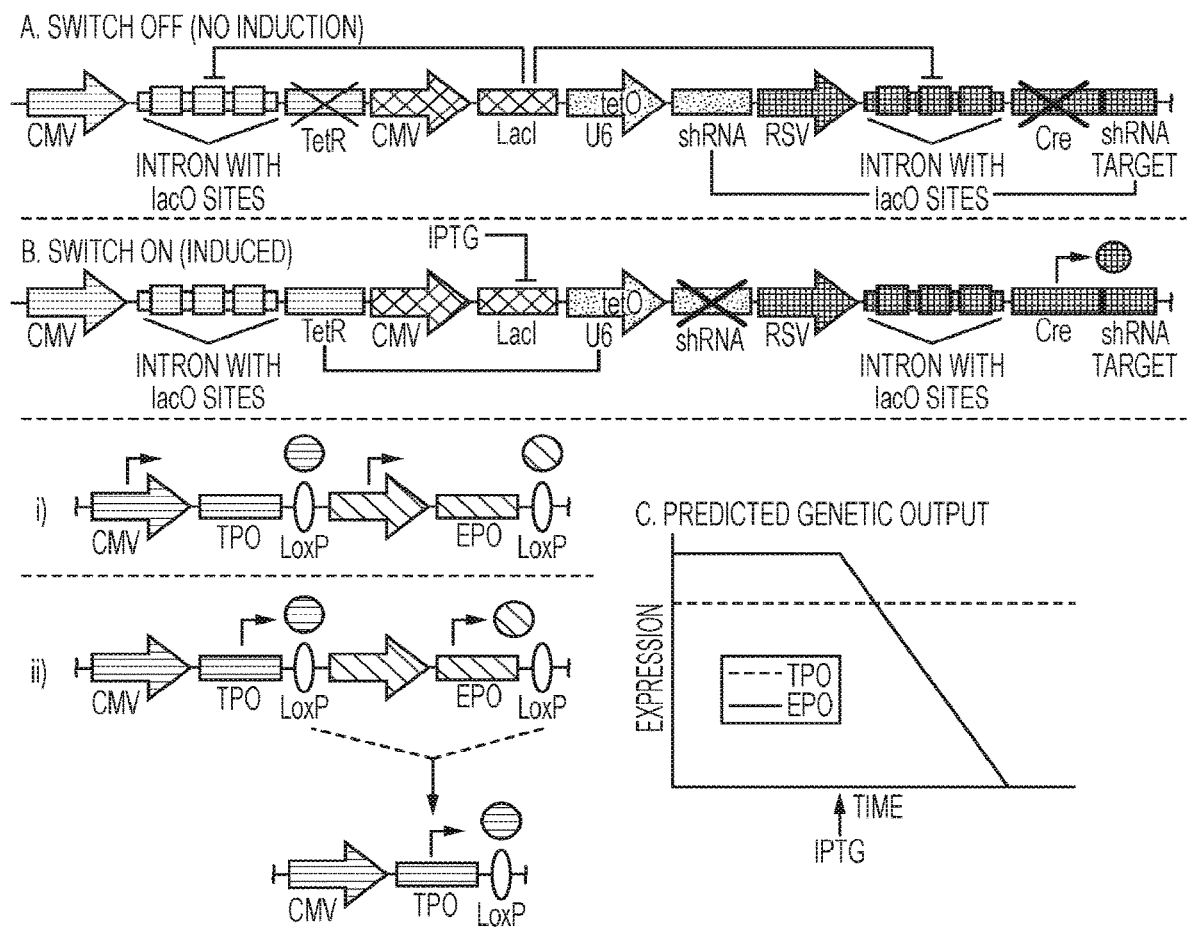
FIGS. 10A-C shows the extrinsic control, removing erythropoietin (EPO).

Experiments and methodology: To better control the differentiation of HSCs to produce platelets, building microenvironments can be built that integrate synthetic biology to enable the dynamic control extrinsic cues. Specifically, tuning the secretion of both TPO and EPO separately from the underlying stromal supporting cells to establish the cooperative or independent interaction between parameters of these cytokines for the purpose of better controlling platelet production (FIG. 8) can be carried out. In this model, OP9 stromal support cells are stably transfected with genetic circuits, which is the most commonly used stromal layer for co-culturing with HSCs to induce their differentiation into MKs. Once the genetic circuits are confirmed, the layer of stably transfected OP9 cells will be mitomycin treated and serve as the stromal layer for primary HSCs. The genetic circuit in the OP9 stromal cells will dynamically control the secretion of EPO and TPO. To better mimic the endosteal niche in the bone marrow microenvironment, mouse femurs are decellularized. Mouse femurs have been decellularized using the previously described protocol. For obtaining HSCs, bone marrow was isolated from both femurs of an adult mouse. RBCs are removed by lysis in ACK buffer and progenitors are sorted on a BD FACS Aria Cell Sorter with PeCy7-Ckit, PerCP5.5-Sca-1, Fitc-Lineage cocktail (BD Biosciences), and Dapi viability stain. Gates are drawn to select Lineage$^-$, Sea$^+$ and K$^+$ cells (LSK cells). 56% of the sorted cells give rise to colonies after 10 days in CFU-methocult assay (Stemcell Technologies) (FIG. 9). After sorting, the LSK cells are plated on the stably transfected OP9 cells in the prepared engineered extrinsic microenvironment and grown in differentiation media where the dynamic secretion of EPO and TPO is controlled by the addition of chemical inducers to the media. The differentiation outcomes of HSCs will be assessed in the following dynamic environments:

1. TPO is constitutively expressed and the expression of EPO is turned off during differentiation. Current studies suggest that the overexpression of TPO drives HSCs to differentiate into platelets, whereas the expression of EPO is important for HSCs to commit to the MEP lineage, however, the continued expression of EPO favors the differentiation into erythrocytes. Using genetic circuits controlling the expression of site-specific Cre recombinase (Cre), the deletion of a DNA sequence flanked by a pair of Cre recognition sequences, called loxP sites, can be controlled. LTRi controlling the expression of Cre has already been established to provide a tight off state where there is no leakage of the transgene. This genetic circuit allows for the constitutive expression of EPO until the circuit is induced with IPTG, causing a homologous recombination event that removes the EPO gene and its promoter (FIG. 10). The differentiation outcome can be determined and the platelets of constitutively expressing TPO can be characterized and upon induction with IPTG, the removal EPO expression. The induced removal of EPO will be done at various time points.

Figures 11A, 11B, 11C:
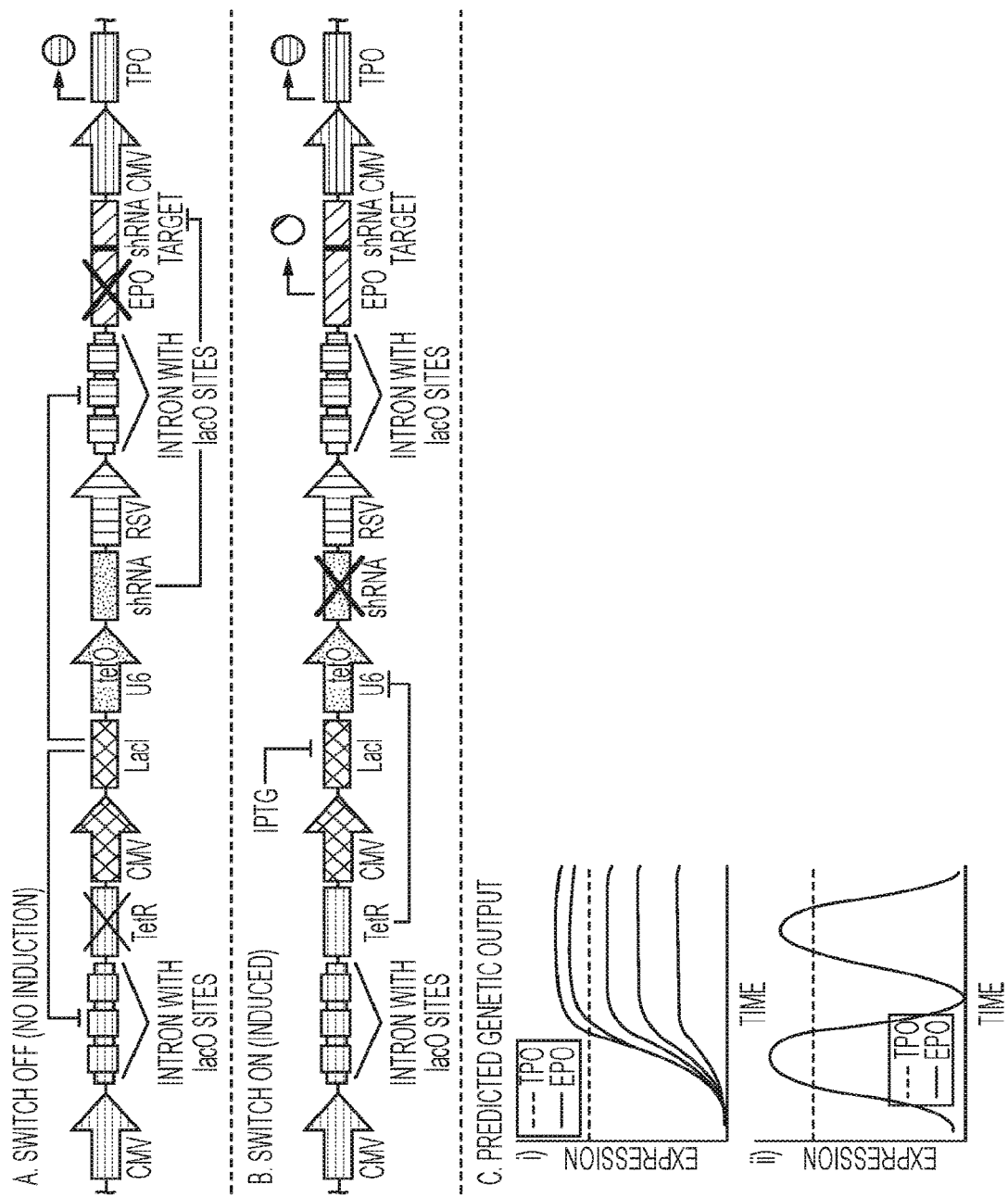
FIGS. 11A-C shows the extrinsic control, tuning erythropoietin (EPO).

2. TPO is constitutively expressed and the expression of EPO is tuned during differentiation. To determine the effects on tuning the level of EPO, a genetic circuit was built that will allow the differentiation outcome of constitutively expressing TPO and tuning the level of EPO at different stages of differentiation (FIG. 11). LTRi has already been established as a rheostat where the level of gene expression can be tuned and turned on and off by the addition of IPTG. Therefore, by adding various amounts of IPTG, the level of EPO expression in the environment can be controlled. The differentiation outcome will be determined and the platelets will be characterized of tuning the level of EPO, in addition to oscillating its expression while TPO is constitutively expressed (FIG. 11). The differentiation characterization will be done at various time points.

Figures 12A, 12B, 12C:
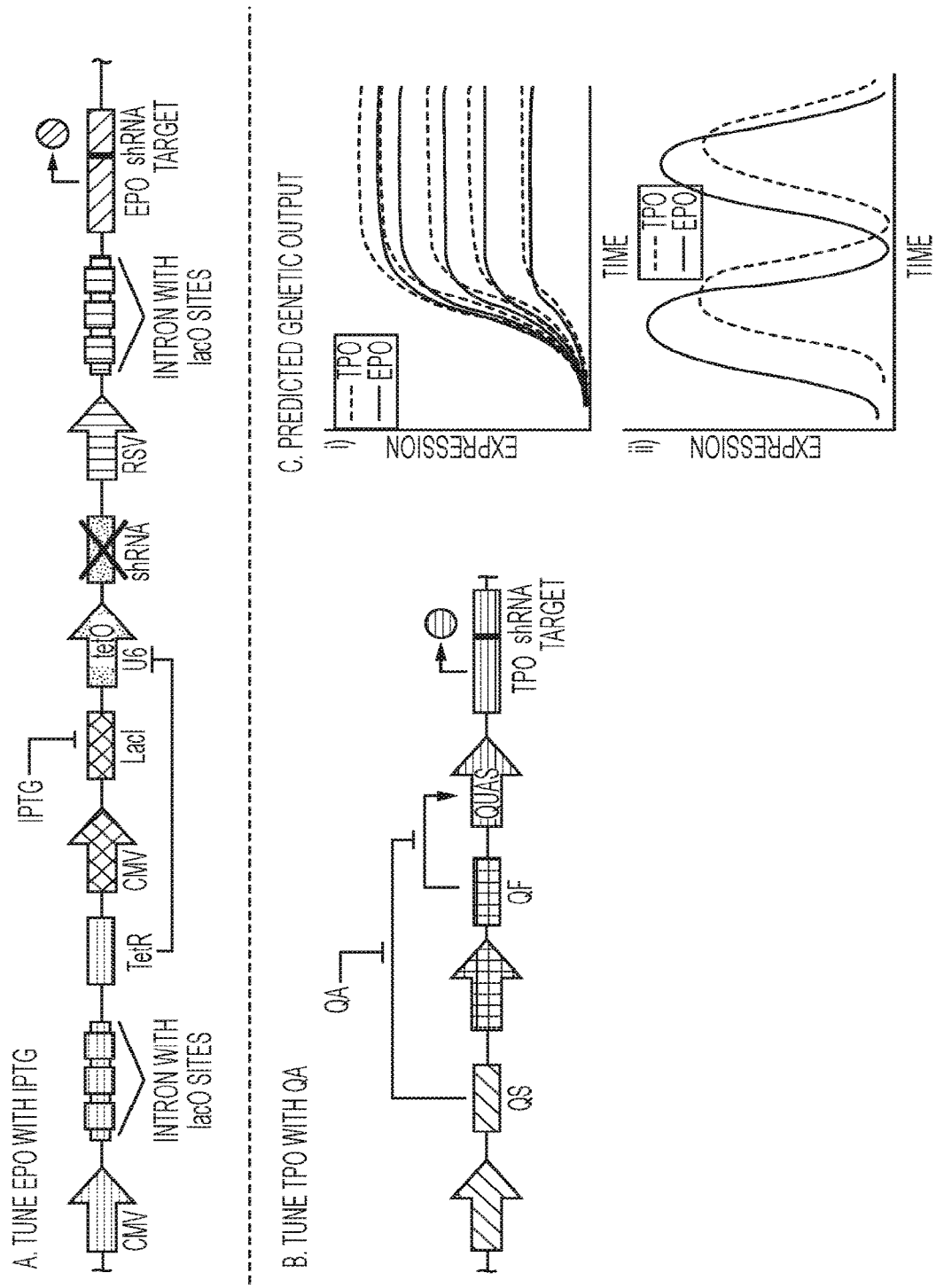
FIGS. 12A-C shows extrinsic control, turning both erythropoietin (EPO) and thrombopoietin (TPO).

3. TPO and EPO are both tuned during differentiation. To determine whether the production of platelets in vitro can be further enhanced, the expression of both TPO and EPO will be changed to determine whether the interplay between these two cytokines has a cooperative or independent effect on platelet production. Using IPTG, the level of EPO expression can be tuned. The Q system in mammalian cells can be engineered and characterized (FIG. 1). Upon completion, both circuits can be independently controlled by adding different inducers to the environment (IPTG and QA). In other words, IPTG and/or QA is added to the media to induce gene expression. The differentiation outcome will be determined and the platelets characterized of tuning the level of both EPO and TPO, in addition to oscillating their expression (FIG. 12). The differentiation characterization will be done at various time points.

4. Assay differentiation outcomes. Stem cell differentiation outcomes will be assessed quantitatively from cell culture with flow cytometry.

a) Determine efficiency of HSCs to differentiate into MKs: To determine the differentiation outcome of dynamically controlling the extrinsic cues HSCs to MKs in vitro, the formation of MKs from HSCs in the extrinsic microenvironment will be test. In these experiments, HSCs will be grown on the OP9 cells containing circuits and conditions described above in STEMspan-ACF medium with STEMspan megakaryocyte expansion supplement (STEMCell Technologies). Cells will be harvested and various times points and analyzed for MK precursor/MK differentiation surface markers: CD13, CD34, CD41a, and CD43 using flow cytometry.

b) Determine efficiency of HSCs to differentiate into platelets: To determine whether dynamically controlling the extrinsic cues alters the differentiation outcome of HSCs to platelets in vitro, the formation of platelets in the extrinsic environment will be tested. After successfully differentiating HSCs into MKs, the insert containing endothelial cells (FIG. 8) will be added and differentiated HSCs into platelets. It is expected that the MKs will extend into the top layer, through the endothelial cells, and release their proplatelets. At different time points, the platelets will be harvested from the top layer by carefully pipetting the media off and purifying them by BSA gradient for analysis of platelet surface markers CD41 a/CD42b using flow cytometry.

5. Platelet characterization. As described above (4), platelet differentiation can be identified by surface markers using flow cytometry. Degranulation and aggregation assessments will be made with respect to known activators von Willebrand Factor (vWF), fibrinogen, collagen, and thrombin. Platelet degranulation will be determined by ELISA specific to serotonin and platelet derived factor 4 (PDF-4). As a control, freshly isolated platelets from mice will be used for comparison. Platelet ability to aggregate in the presence of known activators will be determined using an aggregometer.

Furthermore, platelet activation will be measured by immobilized agonists under realistic 20 ml/hr flow conditions. These established tools mimic platelet roll and transient contact. A microcontact print method can be used to covalently attach known activator to PDMS stamps in a priming region and a downstream platelet capture region. The stamp is otherwise coated in albumin. In the capture region, platelet activation can be microscopically measured to determine adhesion, spreading area, and aggregation. The same system with flow cells containing only immobilized activator or albumin can be used to measure degranulation and activation. The flow chamber eluent is analyzed by FACs for active allbβ3 and P-selectin which specify integrin activation and degranulation, respectively. Additionally, platelet degranulation by thrombin, which acts by enzymatically cleaving PAR receptors on platelets, will be determined by ELISA specific to serotonin and platelet derived factor 4 (PDF-4).

Viruses can be used to transduce the OP9 cells with the genetic circuits described herein. Additionally, the integration technology (FIG. 3) can be used to quickly and efficiently target a location in the genome that allows robust gene expression. While current data strongly suggests that EPO and TPO play a direct role in HSC differentiation to platelets, it is likely that other secreted molecules are involved in this process. All of the synthetic biology tools have been designed and built to be modular, meaning that it is straightforward to swap genes of interest in and out of the genetic circuits. If an increase in MK production can be obtained, but an increase in platelet production is not observed, the top layer can be changed to have a small flow of media across the top to facilitate proplatelet release from the MKs.

6. Mouse embryo fibroblast (MEF) feeder layer. Prior to thawing MEFs, gelatin coated culture vessels are prepared by adding enough 0.1% gelatin solution to evenly cover the surface of the vessel. The gelatin is allowed to adsorb to the tissue culture plastic for at least 5 minutes and then is removed by aspiration prior to seeding MEFs. MEFs are thawed in a 37° C. water bath and immediately transferred to a class II biosafety cabinet. The MEFs are then transferred drop-wise to a 15 ml conical tube containing MEF media. The cells are mixed in the 15 ml conical tube. Next, aliquot is removed to count cells. Pellet cells at 300×g for 5 minutes in a swing bucket rotor. While waiting, the cell count can be determined using a hemocytometer. The cells are removed to the biosafety cabinet and the supernatant is removed by aspiration. Care is taken to not disturb the cell pellet. The pellet is re-suspended with MEF media to achieve a cell seeding density of 15,000-20,000 cells/cm$^2$. The cells are added to gelatin coated plates. The cells are allowed one day to establish a monolayer in a cell culture incubator.

Initiate mouse embryonic stem cell (mESC) cultures. mESCs are thawed in a 37° C. water bath and immediately transferred to a class II biosafety cabinet. MEFs are transferred drop-wise to a 15 ml conical tube containing MEF media. Using MEF media for this step saves on expensive media. Next, the cells are mixed in the 15 ml conical tube. An aliquot can be removed to count cells. Pellet cells at 300×g for 5 minutes in a swing bucket rotor. While waiting, the cell count can be determined using a hemocytometer. The cells are returned to the biosafety cabinet and the supernatant is removed by aspiration. Care is taken to not disturb the cell pellet. The pellet with mESC media is resuspended to achieve a cell seeding density of 3,000-5,000 cells/cm$^2$. The media is removed from MEF culture established 1 day earlier (see above). mESCs are added to the MEF feeder layer and the culture is returned to the incubator.

Maintaining mESCs (can be done daily). The mESC culture is removed from the incubator and work is done in a class II biosafety cabinet. The media is replaced with mESC media. The culture is inspected for colony morphology and confluence. Colonies should be evident two days after seeding. Healthy colonies should appear round with distinct shinny borders. Colonies should not contact other colonies. If colonies appear at risk of touching, they will need to be passaged to avoid differentiation. Overgrown colonies will appear darkened in the center, indicating the presence of necrotic cells. In general mESC cultures need to passed on to freshly prepared MEF feeder layers every 3-4 days. mESCs are passaged by aspirating culture media, followed by a wash (1×) with PBS. 0.1 ml/cm$^2$ of 0.25% trypsin EDTA is added to plates and incubated for 5 minutes. In the biosafety cabinet, the trypsin is neutralized with MEF media (Q.S. 10 ml) in a 15 ml conical tube. An aliquot is removed to count cells. Pellet cells at 300×g for 5 minutes in a swing bucket rotor. While waiting, the cell count can be determined using a hemocytometer. The cells are then returned to the biosafety cabinet and the supernatant is removed by aspiration. Care is taken to not disturb the cell pellet. The pellet is re-suspended with mESC media to achieve a cell seeding density of 30,000-50,000 cells/cm$^2$. The media is removed from the MEF culture established 1 day earlier (see above.). mESCs are added to the MEF feeder layer and the culture is returned to the incubator.

Figure 16:
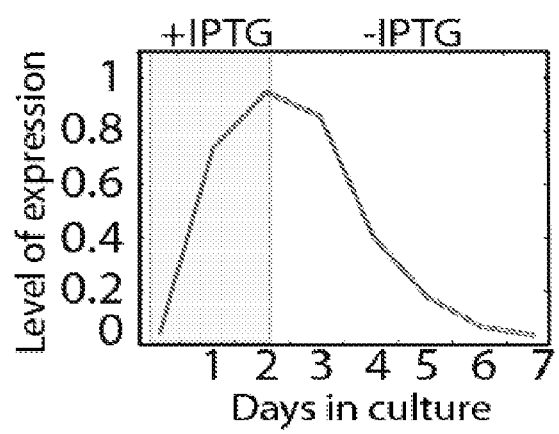
FIG. 16 shows LTRi EGFP in ES cells.

Gene expression induction. 250 μM (final concentration) of IPTG was added to the media. EGFP expression was assessed daily using a flow cytometer (see, FIG. 16).

Figure 17:
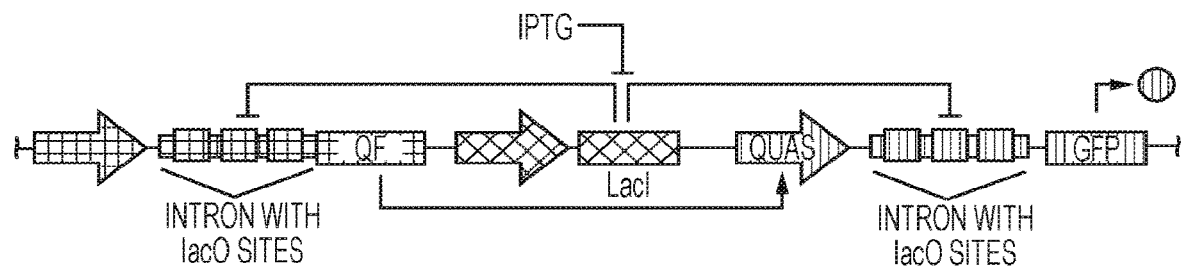
FIG. 17 shows LacQ expression in CHO cells.
Figure 17:
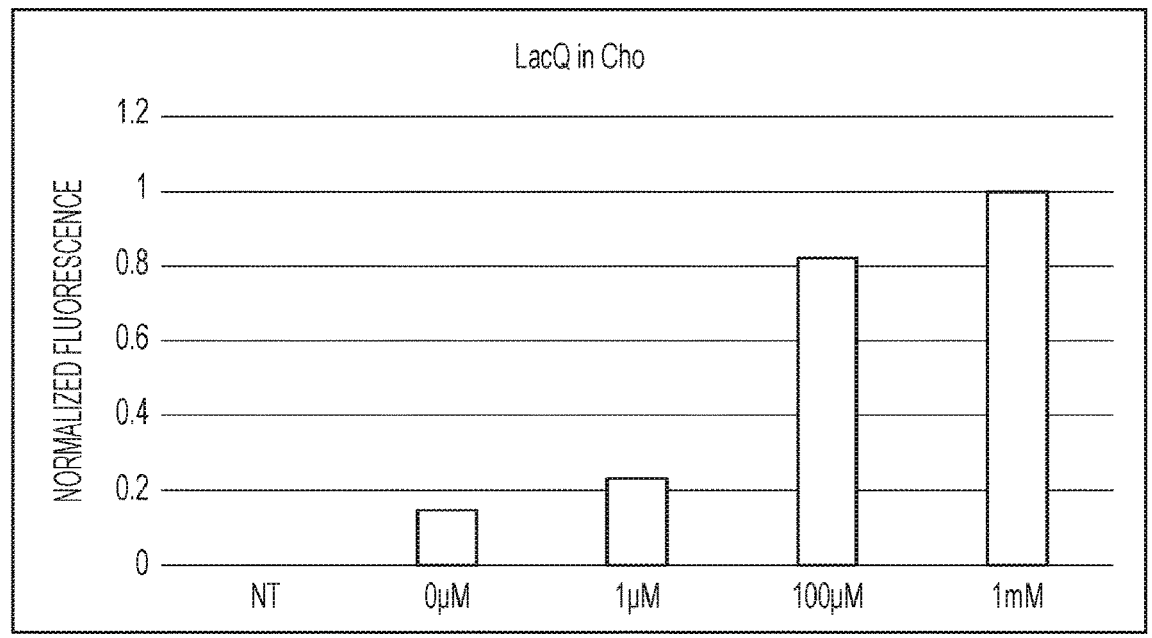

Transfect CHO cells with plasmids. CHO cells were obtained from ATCC and maintained in F12K medium containing 10% FBS and penicillin/streptomycin. Cells were grown in a humidified 5% CO2, 37° C. incubator. The day before transfection, cells were plated in a 12-well plate to ~85% confluency. These cells were transfected with 1.6 μg of expression plasmid using Lipofectamine 2000 reagent (Invitrogen). Twenty-four hours after transfection, cells were washed with PBS, trypsinized, and analyzed by flow cytometry. FIG. 17 shows the genetic circuit and LacQ expression in CHO cells (x-axis indicates the amount of IPTG 24 hours after transfection and gene expression 48 hours after initial transfection using flow cytometer).

Figure 18:
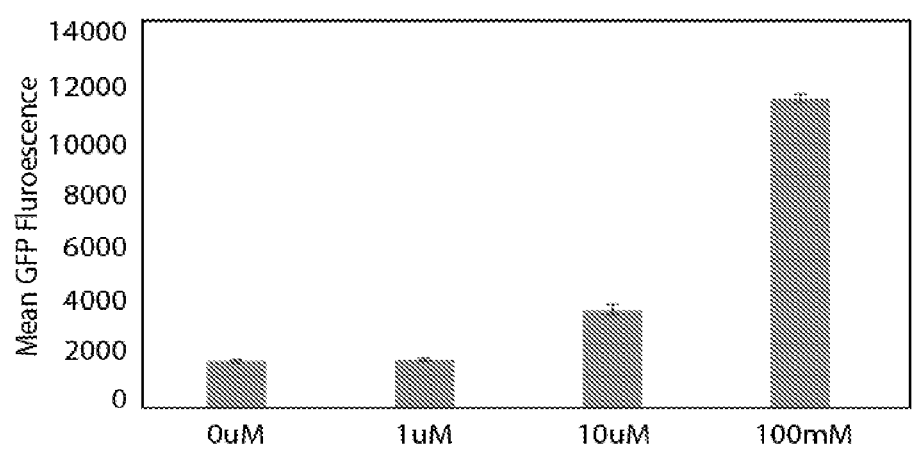
FIG. 18 shows induction of EGFP (using LTRi_EGFP genetic switch) in embryonic stem cells using the specified amount of IPTG (x-axis) after 24 hours of IPTG induction.

FIG. 18 shows the induction of EGFP using LTRi_EGFP genetic switch in embryonic stem cells using the methods for growing and transfecting ES cells and inducing with IPTG as described above.

Figure 19:
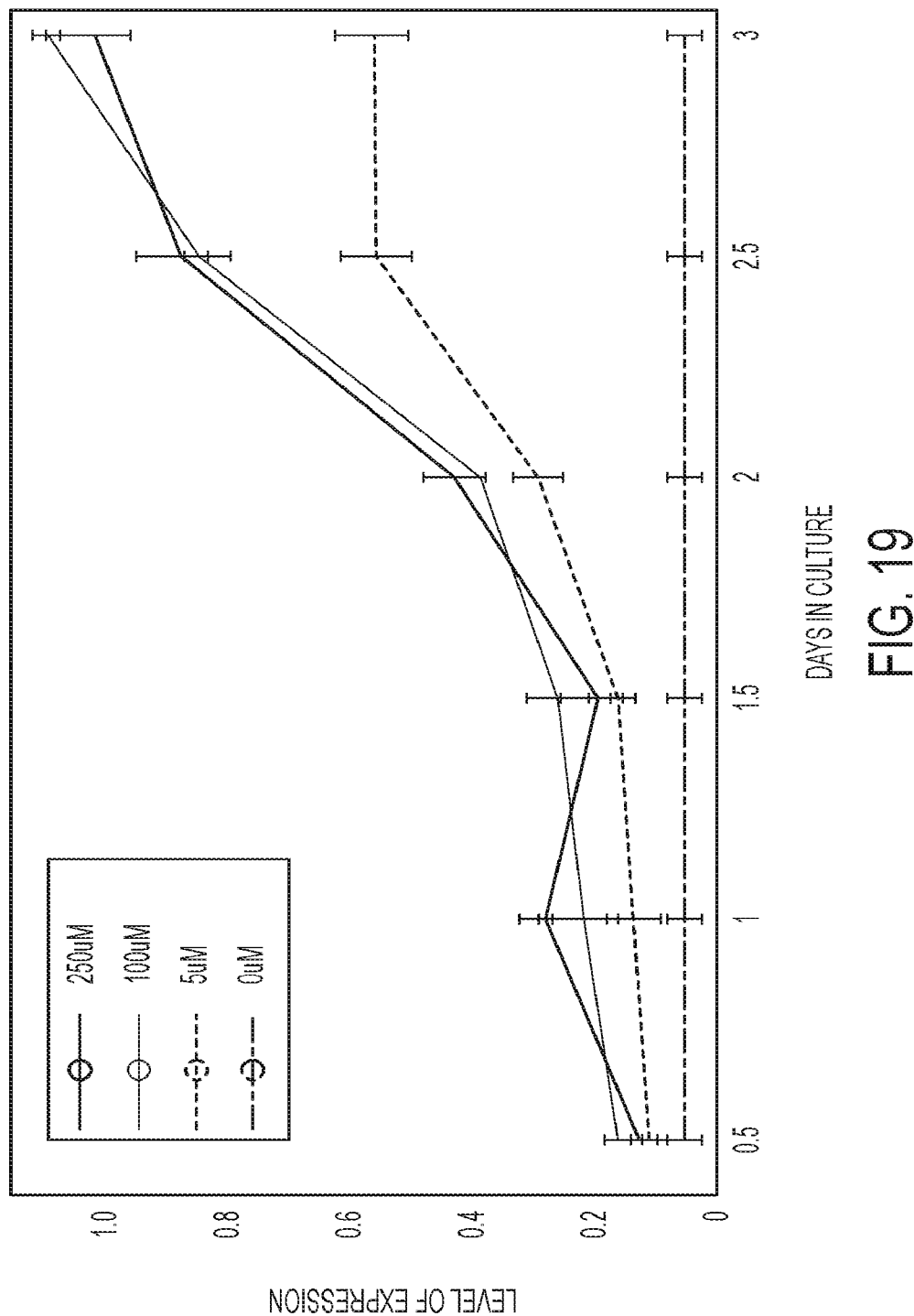
FIG. 19 shows induction of EGFP (using LTRi_EGFP genetic switch) in embryonic stem cells using the specified amount of IPTG up to 3 days of various amounts of IPTG.

FIG. 19 shows the induction of EGFP using LTRi_EGFP genetic switch in embryonic stem cells using the methods of growing and transfecting ES cells and inducing with IPTG as described above.

Example 2: Engineer Pluripotent Stem Cells to Regulate the Intrinsic Cues for Enhanced Differentiation Intrinsic regulation of gene expression is a regulator of cell fate decisions and cell fate decisions are believed to be controlled by the differential expression of lineage-specific transcription factors. Two transcription factors that play an important role in HSC proliferation and MEP lineage specification are HoxB4 and GATA-1, respectively. The expression of HoxB4 has been shown to induce HSC self-renewal, and to be a strong positive regulator of HSC proliferation. HoxB4 has also been shown to induce ES cells to differentiate into HSCs. GATA-1, on the other hand, has been shown to direct HSC differentiation into megakaryocyte lineages. For these reasons, the expression of HoxB4 will be sequentially regulated for enhanced HSC proliferation followed by the activation of GATA-1 to commit these cells to the MK lineage for enhanced platelet production.

Figure 13:
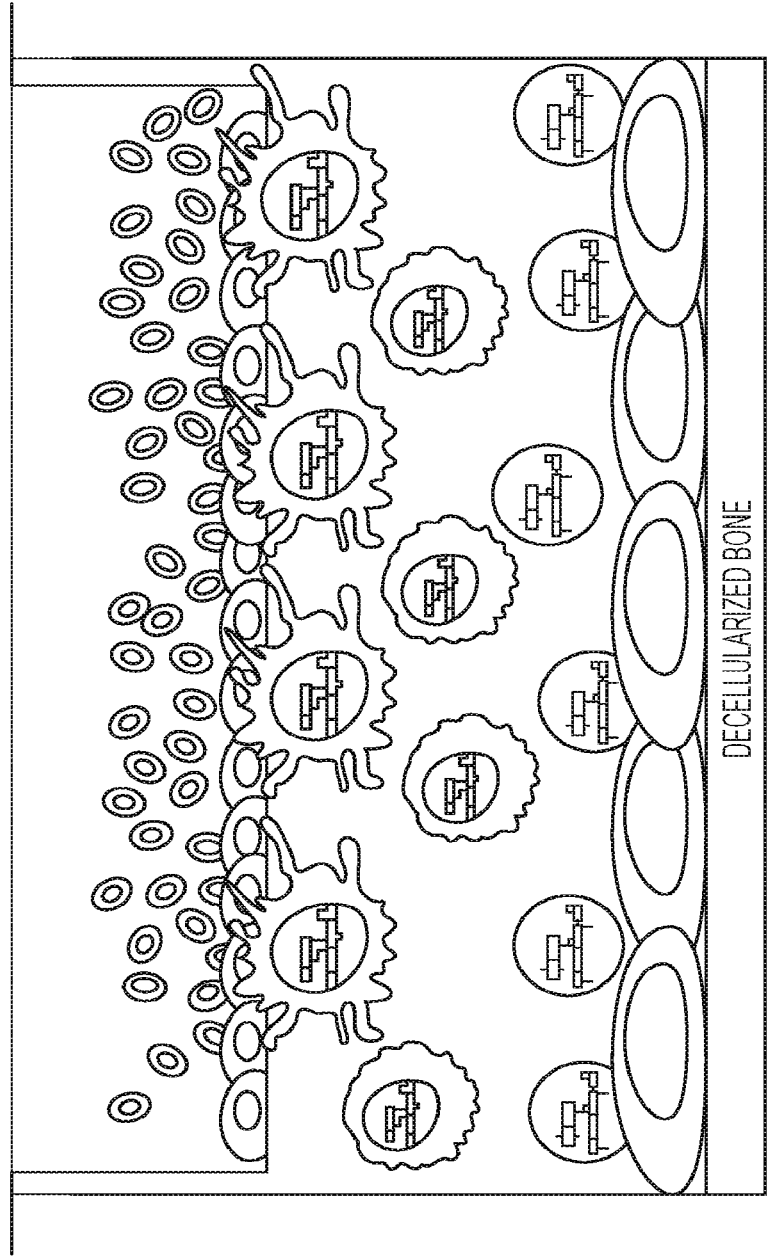
FIG. 13 shows an engineered intrinsic environment in which a transwell system can be used that includes decellularized mouse femurs with OP9 cells grown on top to form the endosteal niche. Hematopoietic stem cells (HSCs) endowed with genetic circuits can be grown and differentiated in this environment.

Experiments and Methodology: To better control the differentiation of HSCs for platelet production, microenvironments can be built that incorporate synthetic biology to dynamically regulate the expression of intrinsic cues. Herein, the intrinsic gene expression events that occur in the bone marrow microenvironment are mimicked by controlling the expression of HoxB4 and GATA-1. Specifically, genetic circuits will regulate their temporal expression during differentiation. For this approach, HSCs will be stably transfected with genetic circuits that control the expansion of the HSC population and promote differentiation to MKs for the enhanced production of platelets. Genetically engineered HSCs will be grown on a layer of mitomycin-C treated OP9 stromal cells (FIG. 13).

Figures 3A, 3B:
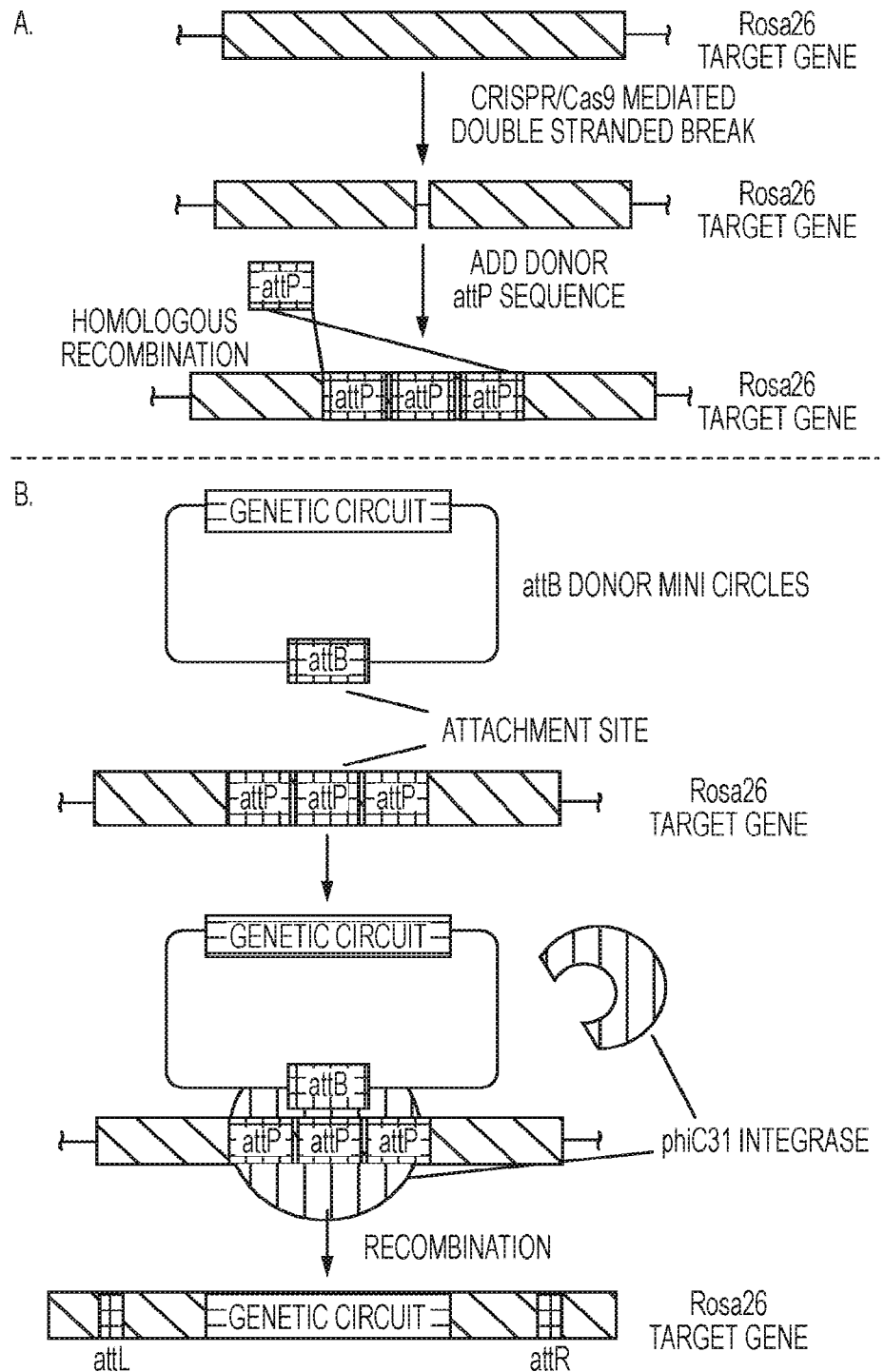
FIGS. 3A-B illustrates targeting the Rosa26 locus for the insertion of genetic circuits.

1. Generation of ES line with three attP sites for circuit integration. To facilitate the introduction of genetic circuits regulating transcription factor expression, CRISPR/Cas9 technology will be used to insert a tandem array of three attP sites at the Rosa26 (R26R) locus (FIG. 3). AttP sites allow the unidirectional insertion of complex genetic circuits specifically at this locale. This is a robust methodology that ensures consistency between different lines and eliminates concerns of positional effects. Furthermore, this approach can be used with ES lines derived from mice of any genetic background. Thus, this technology can be translated into congenic ES cell lines that could be used for studying specific diseases related to platelets including vascular thrombosis models.

Because HSCs are so difficult to grow and to transfect in vitro, genetically engineered ES cells will be produced utilizing phiC31 integrase to insert our genetic circuits regulating HoxB4 and GATA-1 into the 3× attP (FIG. 3). The stably transfected ES cells will be plated on mitomycin-C treated OP9 cells and grown in alpha-MEM medium (Invitrogen) to differentiate the ES cells into HSC progenitors. Controlling HoxB4 and GATA-1 expression will lead to a more homogeneous population of platelets that will result in a higher platelet production to be considered therapeutically relevant for transfusions.

Figures 14A, 14B, 14C:
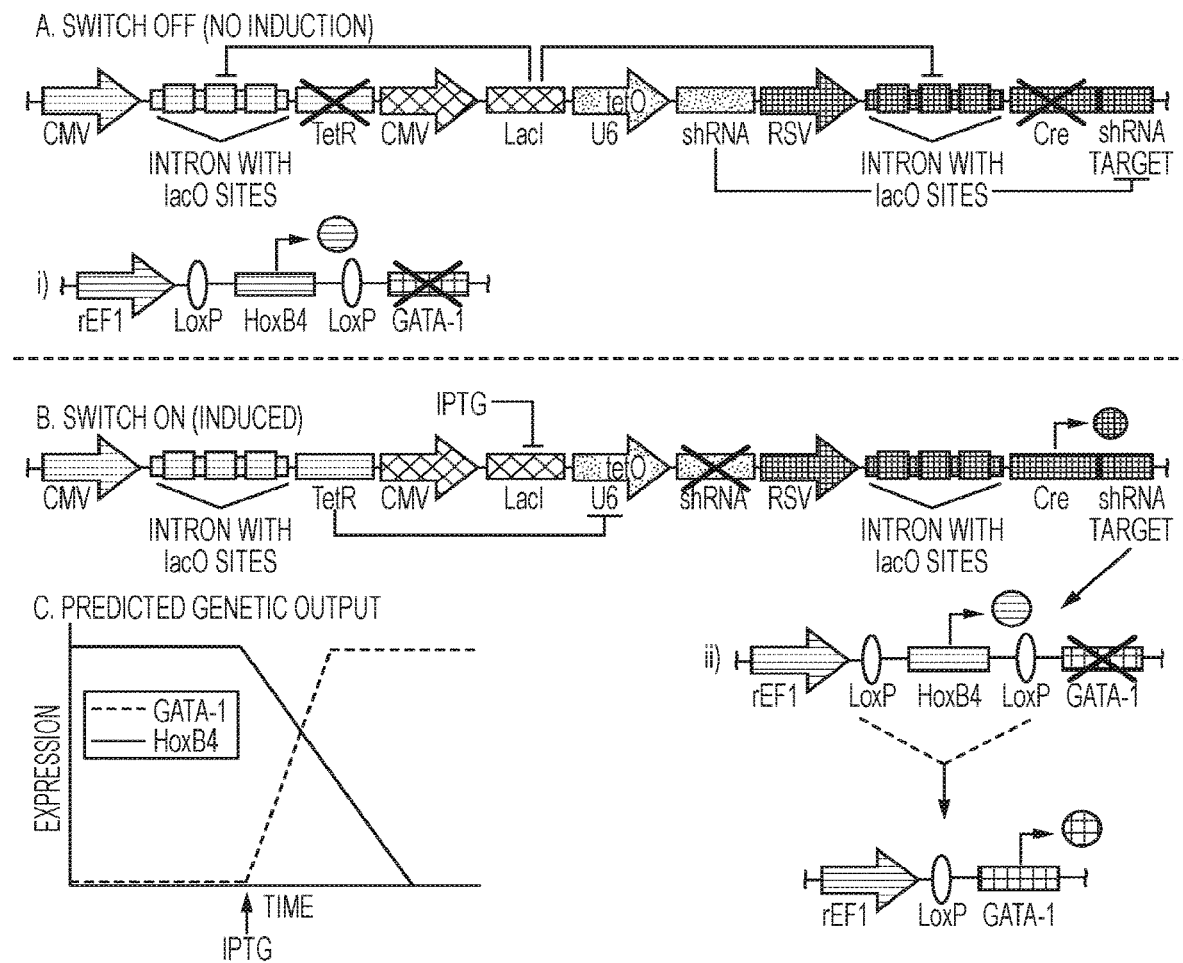
FIGS. 14A-C shows intrinsic control of HoxB4 and GATA-1.

2. HoxB4 is on and GATA-1 is off. Genetic circuits regulating HoxB4 and GATA-1 (FIG. 14) will be integrated into the ES cell genome and grown in the engineered intrinsic environment (FIG. 13). In this circuit, the HoxB4 gene is flanked by two LoxP sites and is constitutively expressed, while GATA-1 is downstream of the LoxP sites and is not expressed. With the addition of IPTG to the media, the expression of Cre is turned on, which causes a homologous recombination event around the LoxP sites, removing the HoxB4 gene and turning on GATA-1 expression (FIG. 14). Once HSCs have expanded, IPTG will be added to the media and the differentiation characterization will be assayed at various time points.

Figure 15A:
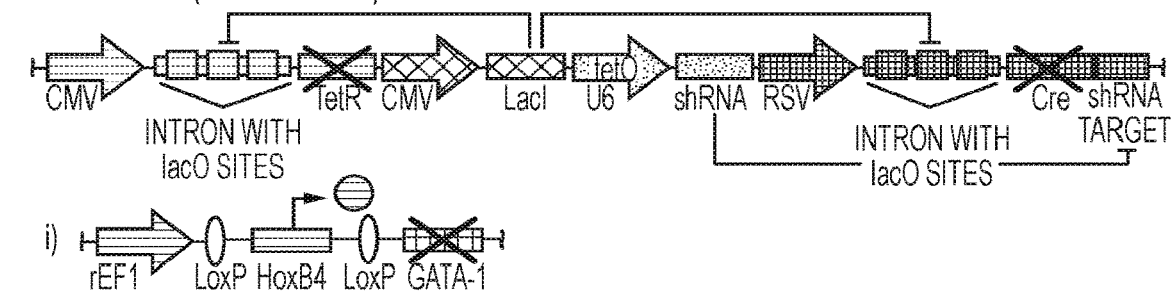
FIGS. 15A-C shows intrinsic control, removing HoxB4, tuning GATA-1.
Figure 15B:
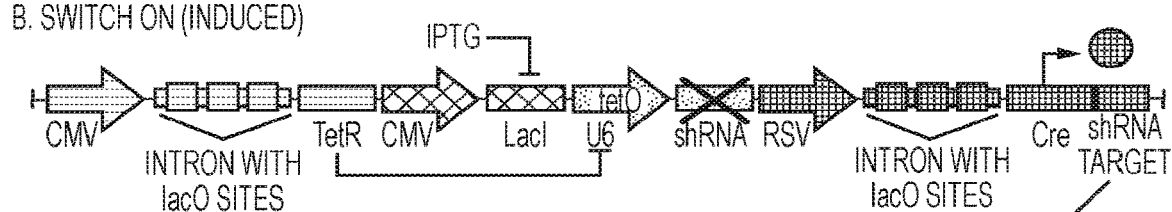
Figure 15C:
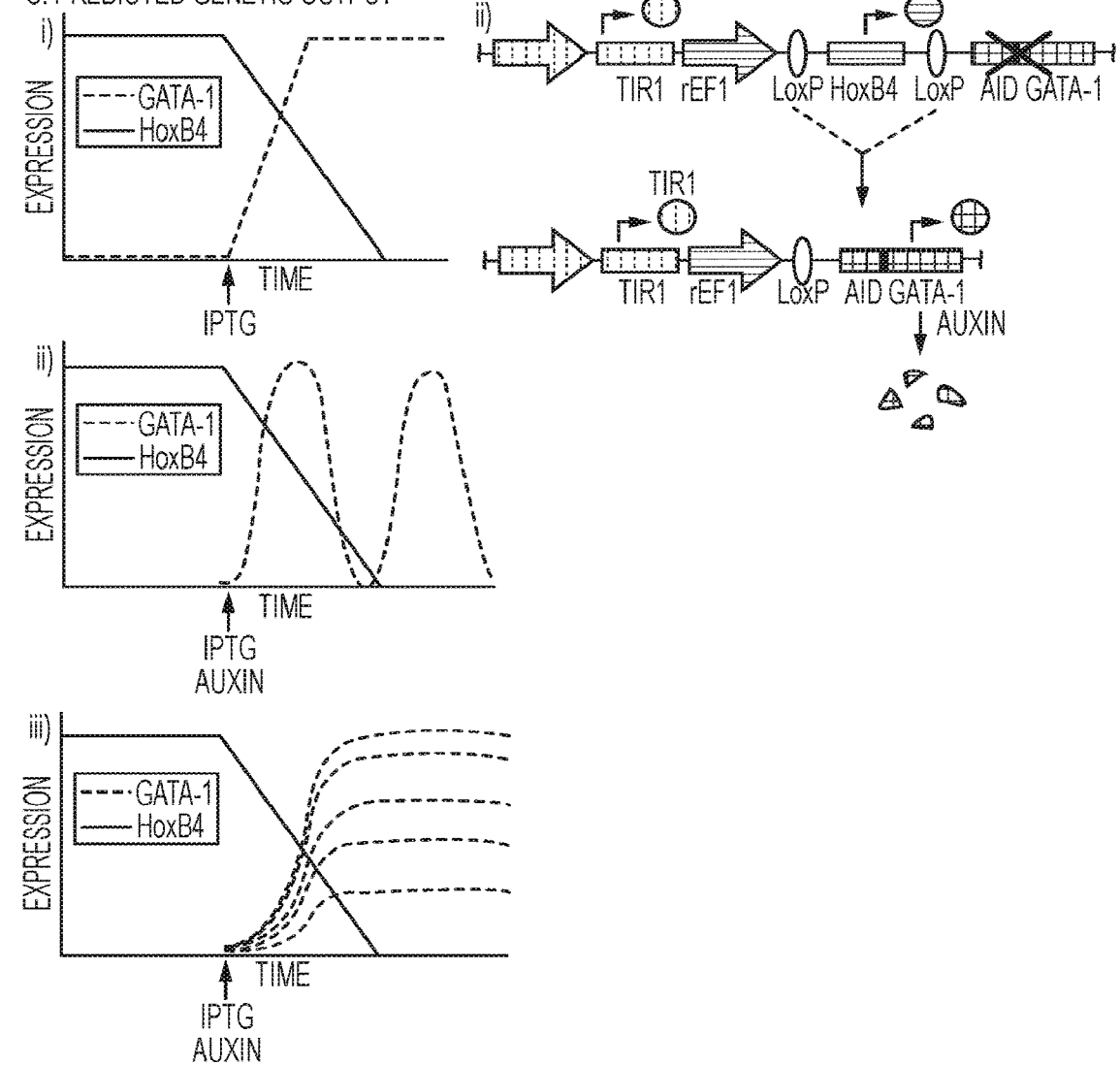
Figure 20:
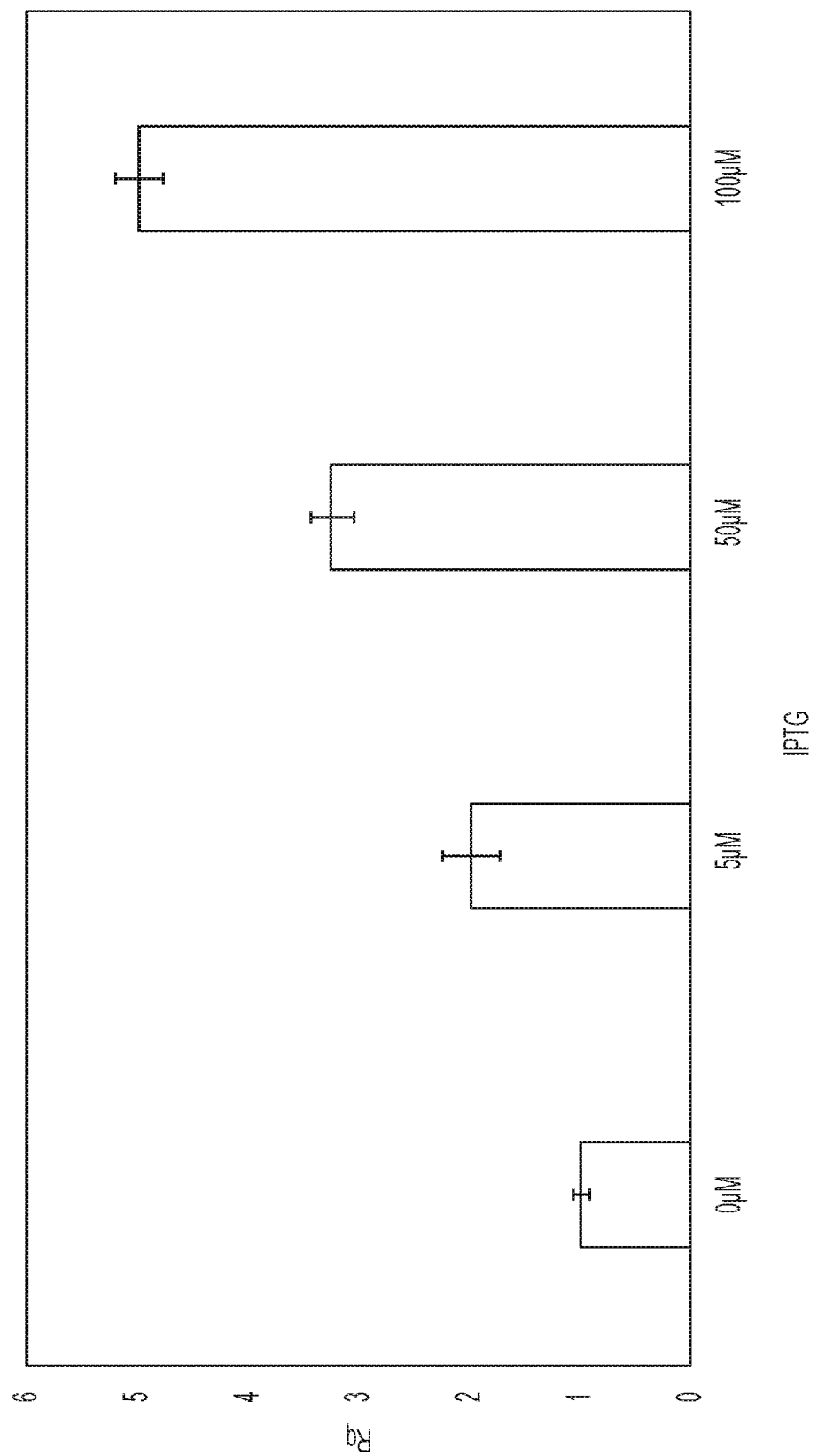
FIG. 20 shows q-RT PCR of HoxB4 mRNA expression with various amount of IPTG.

3. HoxB4 is on and GATA-1 is tuned. Studies indicate that genes are controlled during development and are an important aspect of cell fate decisions. To incorporate this aspect into the in vitro culturing system disclosed herein, the AID protein degradation tag was added to the GATA-1 to enable its rapid degradation upon induction with Auxin (FIG. 15). The induced removal of HoxB4 and the tuning of GATA-1 will be done at various time points. As described herein, the expression patterns (i.e., dynamic patterns—on, off, etc.) are controlled by the inducer. Adding different amounts of genetic inducers to the media results in (and allows for) different levels of gene expression. FIG. 20 shows q-RT PCR of HoxB4 mRNA expression using various amounts of IPTG. The methods for growing and transfecting ES cells and inducing with IPTG are described in Example 1. The LTRi genetic switch was used to drive the expression of HoxB4 (see, FIG. 15).

4. Assay differentiation outcomes. Stem cell differentiation outcomes will be assessed quantitatively from cell culture with flow cytometry.

a) Determine efficiency of ES differentiation to HSCs: To determine the level of HoxB4 expression that enhances the differentiation of ES cells to LSK HSCs in vitro, the differentiation of HSCs will be assessed by quantifying specific cell surface markers using flow cytometry, as described above.

b) Determine efficiency of HSCs to differentiate into platelets: To determine the effects of controlling the intrinsic cues on the differentiation outcome of HSCs to platelets in vitro, the formation of platelets in the extrinsic environment will be tested. After successfully differentiating HSCs into MKs, the insert containing endothelial cells (FIG. 13) will be added and differentiate HSCs into platelets. It is expected that the MKs will extend into the top layer, through the endothelial cells, and release their proplatelets. At different time points we will harvest the platelets from the top layer by carefully pipetting the media off and purifying them by BSA gradient for analysis of platelet surface markers CD41a/CD42b using flow cytometry.

5. Platelet characterization. Platelet differentiation, degranulation, and aggregation will be assessed by the methods mentioned above.

CRISPR/Cas9 complexes and donor 3× attP sequences have been designed with unique restriction sites flanking both sides. These CRISPR/Cas9 complexes have previously shown to target the Rosa26 allele efficiently. Following attP site integration, candidate ES clones will be screened by PCR and restriction digest. In the event that attempts to insert the attP sequence is unsuccessful, the H11 locus will be targeted, which has been shown to function similarly to the Rosa26 locus. Alternatively, the Rosa26 locus will be modified by homologous recombination. Currently, it is unclear whether GATA-1 expression is constitutive after MEPs are formed to direct cells for platelet production (FIG. 7), or whether it needs to be turned off after MEPs are formed from HSC. In the event that an increase erythrocyte production and decrease platelet production is observed using the circuits described (FIG. 14), an AID tag will be placed upstream of GATA-1 to enable the degradation of its protein by adding auxin. This scenario will enable studies to be done to determine whether dynamically controlling GATA-1 will increase platelet production in vitro.

Example 3: Genetically Engineer MKs to Create Platelets That Secrete Biomolecules Platelets possess many characteristics that make them attractive candidates for in vivo delivery of natural and synthetic payloads: 1) they have extensive circulation range in the body, 2) they are a nucleated cells, 3) they are biocompatible, 4) their average lifespan in humans is ~10 days, and 5) following activation, their protein granules serve as secretory vesicles, releasing components to the extracellular fluid. By using synthetic biology as disclosed herein, MKs can be engineered to express therapeutic levels of protein cargo to be targeted for platelet secretion. As a proof of concept, we will express luciferase, enhanced green fluorescence protein (EGFP), and secreted alkaline phosphatase (SEAP) in MKs to determine the efficacy of using platelets as delivery vehicles for therapeutic payloads. This suite of reporter molecules has been selected because they can be used to assay different aspects of the cargo loading and delivery process. GFP will be used to determine if soluble transgenic cargos are packaged into secretory granules, SEAP will be used to assay the extent of cargo release into the circulatory system in mice, and luciferase will be used to determine whether engineering platelets are enriched at sites of injury similar to endogenous platelets.

Experiments and methodology. As a proof of concept to use platelets as delivery vehicles for therapeutic biomolecules, constitutively expressing reporter genes will be inserted into the attP site of ES cells (FIG. 3). These cells will be plated on OP9 stromal support cells and differentiated into MKs using the previously described protocol. Each reporter gene will be assayed for expression to determine the location and function of these recombinantly made proteins and how they affect platelet function:

1. Express GFP in MKs and platelets: Like many potential bio-therapeutic molecules, GFP is a small, soluble protein that diffuses throughout the cytoplasm. In order to determine whether molecules of this class are packed into developing platelets by MKs, the attP landing pad in ES cells will be used that we previously engineered to insert constitutively expressing GFP. These ES cells will be differentiated to MKs on a layer of OP9 stromal cells, which will be harvested for FACS analysis to confirm MKs differentiation, and GFP expression level. The percent of GFP expressing MKs in the whole population will be assessed. After determining the GFP expression level in MKs, MKs expressing GFP will differentiate into platelets. FACs analysis will be done to confirm platelet differentiation and to quantify the GFP expression in these cells. In order to establish the sub-cellular distribution of GFP in platelets, purified cells will be immunolabeled using antibodies against GFP.

2. Express SEAP in MKs and platelets: After differentiating HSCs to MKs on a layer of OP9 stromal cells, these cells will be harvested and quantify SEAP secretion will be quantified in the media using established ELISA protocols. After determining SEAP secretion from MKs, the MKs expressing SEAP will differentiate into platelets and the following in vivo characterization experiments will be conducted:

In vivo characterization: To determine if platelets are capable of secreting biomolecules in vivo, the engineered platelets will be transfused into c57bl/6 mice and test levels of SEAP in the blood will be determined following routine protocols. In short, whole blood will be withdrawn from animals and placed in a tube containing Acid Citrate Dextrose (ACD—1 part ACD in 6 parts whole blood). This will be centrifuged to separate the platelet-rich plasma (PRP), which is centrifuged again to remove the platelet-poor plasma. Wash the RBCs and set aside. Washed engineered platelets containing SEAP will be mixed with the washed RBCs, infused put back into the animal. Blood samples will be taken to quantify the levels of SEAP secretion over many time points.

3. Express luciferase in MKs and platelets: To determine whether the engineered platelets are capable of responding to injury, luciferase in MK cells and platelets will be expressed, which will allow for live animal imaging. After differentiating HSCs into MKs, luciferase activity will be quantified using a plate reader that is capable of bioluminescence. After determining bioluminescence in MKs, w the MKs expressing luciferase will differentiate into platelets and the following in vivo characterization experiments will be conducted:

In vivo characterization: To determine if platelets are capable of responding to injuries in vivo, the engineered platelets will be transfused into c57bl/6 mice and platelet mobilization to sites of injury will be observed. For these experiments, the protocol described above for infusing the engineered platelets disclosed herein into mice will be used. After infusion of the luciferase engineered platelets, longitudinal incisions will be made with a surgical scalpel in the dorsal skin of mice. For bioluminescence imaging in live animals, Luciferin will be added onto the wounds of the animals as previously described and the mice will be imaged for luciferase activity under anesthesia using an IVIS in vivo imaging system (U Utah Cell Imaging Core Facility).

In the event that GFP is not expressed in platelets, we will use myristol-tagged GFP that has been shown to associate with the cell membrane. In this case, the GFP will associate with the MK membrane and is likely to become a part of the platelet membrane. Microscopy and flow cytometry will be done to observe and quantify GFP expression.

In the event that SEAP or luciferase are not a part of the platelets, these reporter genes can be tagged with the amino acid sequence, LKNG (SEQ ID NO: 1), which has been demonstrated to be directly involved in the targeting and/or storage of the megakaryocytic proteins. To accomplish this, the LKNG sequence (SEQ ID NO: 1) can be fused to the reporter molecules in either the 5' or 3' UTR to be targeted for granule packaging in MKs.

Induced pluripotent stem cells have the potential to provide a replenishable source of on-demand, patient-matched platelets for transfusions. With this in mind, synthetic biology as described herein can be used to develop tools that can be used to reprogram patient-specific HSCs.

REFERENCES

NHLBI, Stem Cell-Derived Blood Products for Therapeutic Use, RFA-HL-15-022, (2014).

K. R. Machlus, J. E. Italiano, Jr., The incredible journey: From megakaryocyte development to platelet formation, The Journal of cell biology, 201 (2013) 785-796.

J. Cid, M. Lozano, Platelet dose for prophylactic platelet transfusions, Expert review of hematology, 3 (2010) 397-400.

T. T. Fujimoto, S. Kohata, H. Suzuki, H. Miyazaki, K. Fujimura, Production of functional platelets by differentiated embryonic stem (ES) cells in vitro, Blood, 102 (2003) 4044-4051.

Q. Feng, N. Shabrani, J. N. Thon, H. Huo, A. Thiel, K. R. Machlus, K. Kim, J. Brooks, F. Li, C. Luo, E. A. Kimbrel, J. Wang, K. S. Kim, J. Italiano, J. Cho, S. J. Lu, R. Lanza, Scalable generation of universal platelets from human induced pluripotent stem cells, Stem cell reports, 3 (2014) 817-831.

O. Klimchenko, M. Mori, A. Distefano, T. Langlois, F. Larbret, Y. Lecluse, O. Feraud, W. Vainchenker, F. Norol, N. Debili, A common bipotent progenitor generates the erythroid and megakaryocyte lineages in embryonic stem cell-derived primitive hematopoiesis, Blood, 114 (2009) 1506-1517.

N. Takayama, H. Nishikii, J. Usui, H. Tsukui, A. Sawaguchi, T. Hiroyama, K. Eto, H. Nakauchi, Generation of functional platelets from human embryonic stem cells in vitro via ES-sacs, VEGF-promoted structures that concentrate hematopoietic progenitors, Blood, 111 (2008) 5298-5306.

S. J. Lu, F. Li, H. Yin, Q. Feng, E. A. Kimbrel, E. Hahm, J. N. Thon, W. Wang, J. E. Italiano, J. Cho, R. Lanza, Platelets generated from human embryonic stem cells are functional in vitro and in the microcirculation of living mice, Cell research, 21 (2011) 530-545.

Y. Ono, Y. Wang, H. Suzuki, S. Okamoto, Y. Ikeda, M. Murata, M. Poncz, Y. Matsubara, Induction of functional platelets from mouse and human fibroblasts by p45NF-E2/Maf, Blood, 120 (2012) 3812-3821.

R. M. Kaufman, R. Airo, S. Pollack, W. H. Crosby, Circulating megakaryocytes and platelet release in the lung, Blood, 26 (1965) 720-731.

S. H. Orkin, L. I. Zon, Hematopoiesis: an evolving paradigm for stem cell biology, Cell, 132 (2008) 631-644.

L. I. Zon, Intrinsic and extrinsic control of haematopoietic stem-cell self-renewal, Nature, 453 (2008) 306-313.

J. W. Chin, Programming and engineering biological networks, Current opinion in structural biology, 16 (2006) 551-556.

T. K. Lu, A. S. Khalil, J. J. Collins, Next-generation synthetic gene networks, Nature biotechnology, 27 (2009) 1139-1150.

S. Mukherji, A. van Oudenaarden, Synthetic biology: understanding biological design from synthetic circuits, Nature reviews. Genetics, 10 (2009) 859-871.

A. L. Slusarczyk, A. Lin, R. Weiss, Foundations for the design and implementation of synthetic genetic circuits, Nature reviews. Genetics, 13 (2012) 406-420.

P. Siuti, J. Yazbek, T. K. Lu, Synthetic circuits integrating logic and memory in living cells, Nature biotechnology, 31 (2013) 448-452.

A. E. Friedland, T. K. Lu, X. Wang, D. Shi, G. Church, J. J. Collins, Synthetic gene networks that count, Science, 324 (2009) 1199-1202.

Z. Xie, L. Wroblewska, L. Prochazka, R. Weiss, Y. Benenson, Multi-input RNAi-based logic circuit for identification of specific cancer cells, Science, 333 (2011) 1307-1311.

Y. Y. Chen, M. C. Jensen, C. D. Smolke, Genetic control of mammalian T-cell proliferation with synthetic RNA regulatory systems, Proceedings of the National Academy of Sciences of the United States of America, 107 (2010) 8531-8536.

J. W. Kotula, S. J. Kerns, L. A. Shaket, L. Siraj, J. J. Collins, J. C. Way, P. A. Silver, Programmable bacteria detect and record an environmental signal in the mammalian gut, Proceedings of the National Academy of Sciences of the United States of America, 111 (2014) 4838-4843.

T. S. Gardner, C. R. Cantor, J. J. Collins, Construction of a genetic toggle switch in *Escherichia coli*, Nature, 403 (2000) 339-342.

M. B. Elowitz, S. Leibler, A synthetic oscillatory network of transcriptional regulators, Nature, 403 (2000) 335-338.

A. Becskei, L. Serrano, Engineering stability in gene networks by autoregulation, Nature, 405 (2000) 590-593.

T. L. Deans, C. R. Cantor, J. J. Collins, A tunable genetic switch based on RNAi and repressor proteins for regulating gene expression in mammalian cells, Cell, 130 (2007) 363-372.

T. L. Deans, A. Singh, M. Gibson, J. H. Elisseeff, Regulating synthetic gene networks in 3D materials, Proceedings of the National Academy of Sciences of the United States of America, 109 (2012) 15217-15222.

C. J. Potter, B. Tasic, E. V. Russler, L. Liang, L. Luo, The Q system: a repressible binary system for transgene expression, lineage tracing, and mosaic analysis, Cell, 141 (2010) 536-548.

A. Subedi, M. Macurak, S. T. Gee, E. Monge, M. G. Goll, C. J. Potter, M. J. Parsons, M. E. Halpern, Adoption of the Q transcriptional regulatory system for zebrafish transgenesis, Methods, 66 (2014) 433-440.

K. Nishimura, T. Fukagawa, H. Takisawa, T. Kakimoto, M. Kanemaki, An auxin-based degron system for the rapid depletion of proteins in nonplant cells, Nature methods, 6 (2009) 917-922.

S. Casola, Mouse models for miRNA expression: the ROSA26 locus, Methods in molecular biology, 667 (2010) 145-163.

B. Tasic, S. Hippenmeyer, C. Wang, M. Gamboa, H. Zong, Y. Chen-Tsai, L. Luo, Site-specific integrase-mediated transgenesis in mice via pronuclear injection, Proceedings of the National Academy of Sciences of the United States of America, 108 (2011) 7902-7907.

J. Antonchuk, G. Sauvageau, R. K. Humphries, HOXB4-induced expansion of adult hematopoietic stem cells ex vivo, Cell, 109 (2002) 39-45.

M. Kyba, R. C. Perlingeiro, G. Q. Daley, HoxB4 confers definitive lymphoid-myeloid engraftment potential on embryonic stem cell and yolk sac hematopoietic progenitors, Cell, 109 (2002) 29-37.

P. L. Mok, S. K. Cheong, C. F. Leong, A. Othman, In vitro expression of erythropoietin by transfected human mesenchymal stromal cells, Cytotherapy, 10 (2008) 116-124.

D. Metcalf, Hematopoietic cytokines, Blood, 111 (2008) 485-491.

A. Grover, E. Mancini, S. Moore, A. J. Mead, D. Atkinson, K. D. Rasmussen, D. O'Carroll, S. E. Jacobsen, C. Nerlov, Erythropoietin guides multipotent hematopoietic progenitor cells toward an erythroid fate, The Journal of experimental medicine, 211 (2014) 181-188.

T. Abe, Y. Takaue, Y. Kawano, Y. Kuroda, Effect of recombinant erythropoietin in interaction with stromal factors on cord blood hematopoiesis, Blood, 87 (1996) 3212-3217.

L. Gutierrez, S. Tsukamoto, M. Suzuki, H. Yamamoto-Mukai, M. Yamamoto, S. Philipsen, K. Ohneda, Ablation of Gata1 in adult mice results in aplastic crisis, revealing its essential role in steady-state and stress erythropoiesis, Blood, 111 (2008) 4375-4385.

H. Iwasaki, S. Mizuno, R. A. Wells, A. B. Cantor, S. Watanabe, K. Akashi, GATA-1 converts lymphoid and myelomonocytic progenitors into the megakaryocyte/erythrocyte lineages, Immunity, 19 (2003) 451-462.

V. R. Deutsch, A. Tomer, Megakaryocyte development and platelet production, British journal of haematology, 134 (2006) 453-466.

Y. Chang, D. Bluteau, N. Debili, W. Vainchenker, From hematopoietic stem cells to platelets, Journal of thrombosis and haemostasis: JTH, 5 Suppl 1 (2007) 318-327.

L. Fugger, M. A. Friese, J. I. Bell, From genes to function: the next challenge to understanding multiple sclerosis, Nature reviews. Immunology, 9 (2009) 408-417.

Y. M. Mosaad, Hematopoietic stem cells: an overview, Transfusion and apheresis science: official journal of the World Apheresis Association: official journal of the European Society for Haemapheresis, 51 (2014) 68-82.

S. Assou, I. Boumela, D. Haouzi, T. Anahory, H. Dechaud, J. De Vos, S. Hamamah, Dynamic changes in gene expression during human early embryo development: from fundamental aspects to clinical applications, Human reproduction update, 17 (2011) 272-290.

A. Aulehla, O. Pourquie, Oscillating signaling pathways during embryonic development, Current opinion in cell biology, 20 (2008) 632-637.

C. Y. Chen, Y. Yamashita, T. C. Chang, A. Yamashita, W. Zhu, Z. Zhong, A. B. Shyu, Versatile applications of transcriptional pulsing to study mRNA turnover in mammalian cells, Rna, 13 (2007) 1775-1786.

H. W. Chen, S. L. Yu, W. J. Chen, P. C. Yang, C. T. Chien, H. Y. Chou, H. N. Li, K. Peck, C. H. Huang, F. Y. Lin, J. J. Chen, Y. T. Lee, Dynamic changes of gene expression profiles during postnatal development of the heart in mice, Heart, 90 (2004) 927-934.

J. R. Chubb, T. Trcek, S. M. Shenoy, R. H. Singer, Transcriptional pulsing of a developmental gene, Current biology: CB, 16 (2006) 1018-1025.

S. Handwerger, B. Aronow, Dynamic changes in gene expression during human trophoblast differentiation, Recent progress in hormone research, 58 (2003) 263-281.

M. G. Haugh, E. G. Meyer, S. D. Thorpe, T. Vinardell, G. P. Duffy, D. J. Kelly, Temporal and spatial changes in cartilage-matrix-specific gene expression in mesenchymal stem cells in response to dynamic compression, Tissue engineering. Part A, 17 (2011) 3085-3093.

S. Iyer-Biswas, F. Hayot, C. Jayaprakash, Stochasticity of gene products from transcriptional pulsing, Physical review. E, Statistical, nonlinear, and soft matter physics, 79 (2009) 031911.

M. Y. Lo, S. Rival-Gervier, P. Pasceri, J. Ellis, Rapid transcriptional pulsing dynamics of high expressing retroviral transgenes in embryonic stem cells, PloS one, 7 (2012) e37130.

M. Messerle, M. Follo, M. Nehls, H. Eggert, T. Boehm, Dynamic changes in gene expression during in vitro differentiation of mouse embryonic stem cells, Cytokines and molecular therapy, 1 (1995) 139-143.

N. Suzuki, C. Furusawa, K. Kaneko, Oscillatory protein expression dynamics endows stem cells with robust differentiation potential, PloS one, 6 (2011) e27232.

D. J. Kuter, G. J. Mufti, B. J. Bain, R. P. Hasserjian, W. Davis, M. Rutstein, Evaluation of bone marrow reticulin formation in chronic immune thrombocytopenia patients treated with romiplostim, Blood, 114 (2009) 3748-3756.

D. J. Kuter, Biology and chemistry of thrombopoietic agents, Seminars in hematology, 47 (2010) 243-248.

W. L. Grayson, S. Bhumiratana, C. Cannizzaro, P. H. Chao, D. P. Lennon, A. I. Caplan, G. Vunjak-Novakovic, Effects of initial seeding density and fluid perfusion rate on formation of tissue-engineered bone, Tissue engineering. Part A, 14 (2008) 1809-1820.

N. Sternberg, D. Hamilton, Bacteriophage P1 site-specific recombination. I. Recombination between loxP sites, Journal of molecular biology, 150 (1981) 467-486.

M. Stetler-Stevenson, D. C. Arthur, N. Jabbour, X. Y. Xie, J. Molldrem, A. J. Barrett, D. Venzon, M. E. Rick, Diagnostic utility of flow cytometric immunophenotyping in myelodysplastic syndrome, Blood, 98 (2001) 979-987.

A. Robert, V. Cortin, A. Gamier, N. Pineault, Megakaryocyte and platelet production from human cord blood stem cells, Methods in molecular biology, 788 (2012) 219-247.

J. L. Miller, J. M. Kupinski, A. Castella, Z. M. Ruggeri, von Willebrand factor binds to platelets and induces aggregation in platelet-type but not type IIB von Willebrand disease, The Journal of clinical investigation, 72 (1983) 1532-1542.

D. P. Mikhailidis, M. A. Barradas, A. Maris, J. Y. Jeremy, P. Dandona, Fibrinogen mediated activation of platelet aggregation and thromboxane A2 release: pathological implications in vascular disease, Journal of clinical pathology, 38 (1985) 1166-1171.

R. L. Katzman, A. H. Kang, E. H. Beachey, Collagen-induced platelet aggregation: involvement of an active glycopeptide fragment (alpha1-CB5), Science, 181 (1973) 670-672.

R. Muggli, Collagen-induced platelet aggregation: native collagen quaternary structure is not an essential structural requirement, Thrombosis research, 13 (1978) 829-843.

V. Ramakrishnan, F. DeGuzman, M. Bao, S. W. Hall, L. L. Leung, D. R. Phillips, A thrombin receptor function for platelet glycoprotein Ib-IX unmasked by cleavage of glycoprotein V, Proceedings of the National Academy of Sciences of the United States of America, 98 (2001) 1823-1828.

M. Ungerer, M. Peluso, A. Gillitzer, S. Massberg, U. Heinzmann, C. Schulz, G. Munch, M. Gawaz, Generation of functional culture-derived platelets from CD34+ progenitor cells to study transgenes in the platelet environment, Circulation research, 95 (2004) e36-44.

L. E. Corum, V. Hlady, Screening platelet-surface interactions using negative surface charge gradients, Biomaterials, 31 (2010) 3148-3155.

L. E. Corum, V. Hlady, The effect of upstream platelet-fibrinogen interactions on downstream adhesion and activation, Biomaterials, 33 (2012) 1255-1260.

R. J. Westrick, M. E. Winn, D. T. Eitzman, Murine models of vascular thrombosis (Eitzman series), Arteriosclerosis, thrombosis, and vascular biology, 27 (2007) 2079-2093.

S. Hippenmeyer, Y. H. Youn, H. M. Moon, K. Miyamichi, H. Zong, A. Wynshaw-Boris, L. Luo, Genetic mosaic dissection of Lis1 and Ndel1 in neuronal migration, Neuron, 68 (2010) 695-709.

H. Ye, M. Daoud-El Baba, R. W. Peng, M. Fussenegger, A synthetic optogenetic transcription device enhances blood-glucose homeostasis in mice, Science, 332 (2011) 1565-1568.

N. Wu, E. D. Jansen, J. M. Davidson, Comparison of mouse matrix metalloproteinase 13 expression in free-electron laser and scalpel incisions during wound healing, The Journal of investigative dermatology, 121 (2003) 926-932.

J. M. Rhee, M. K. Pirity, C. S. Lackan, J. Z. Long, G. Kondoh, J. Takeda, A. K. Hadjantonakis, In vivo imaging and differential localization of lipid-modified GFP-variant fusions in embryonic stem cells and mice, Genesis, 44 (2006) 202-218.

N. El Golli, O. Issertial, J. P. Rosa, V. Briquet-Laugier, Evidence for a granule targeting sequence within platelet factor 4, The Journal of biological chemistry, 280 (2005) 30329-30335.

What is claimed is:

1. A method of producing a platelet or red blood cell comprising a therapeutic peptide, the method comprising:
   a) providing a feeder cell;
   b) providing a genetically engineered fed cell, wherein the genetically engineered fed cell comprises
      i) a first genetic circuit, wherein the first genetic circuit comprises GATA-1 and/or HoxB4, one or more recombination sites, one or more recombinases, and one or more promoters operably linked to the GATA-1 and/or HoxB4, one or more recombination sites and one or more recombinases; and
      ii) a second genetic circuit, wherein the second genetic circuit comprises a gene of interest capable of encoding a therapeutic peptide, one or more recombination sites, one or more recombinases, and one or more promoters operably linked to the gene of interest, one or more recombination sites and one or more recombinases;
   c) culturing the feeder cell in a) with the genetically engineered fed cell in b) in a media under conditions that permit the genetically engineered fed cell to differentiate into platelet progenitor stem cells and/or differentiate into red blood progenitor stem cells and to express the gene of interest; and
   d) producing the platelet progenitor stem cells and/or red blood progenitor stem cells comprising the therapeutic peptide encoded by the gene of interest.

2. The method of claim 1, further comprising:
   e) re-culturing the platelet progenitor stem cells and/or red blood progenitor stem cells of step c) in a media under conditions promoting the differentiation of the platelet progenitor stem cells into platelets and/or the red blood progenitor stem cells into red blood cells.

3. The method of claim 2, further comprising:
   f) collecting and isolating the platelets and red blood cells.

4. The method of claim 1, wherein the first genetic circuit and second genetic circuit are regulated by one or more media modulators.

5. The method of claim 4, wherein the one or more media modulators are isopropyl β-D-1-thiogalactopyranoside (IPTG), tetracycline, doxycycline, quinic acid, or auxin.

6. The method of claim 1, wherein the one or more promoters of the first genetic circuit or second genetic circuit are a CMV, a RSV and/or a U6 promoter.

7. The method of claim 1, wherein the first genetic circuit and second genetic circuit are operably linked to and regulated by the one or more promoters.

8. The method of claim 1, wherein the one or more recombinases is Cre or phiC31 integrase.

9. The method of claim 1, wherein the one or more recombination sites are loxP attP or Bxb1.

10. The method of claim 9, wherein the attP, loxP, or Bxb1 recombination sites are inserted at Rosa26 locus.

11. The method of claim 1, wherein the one or more recombination sites serve as an insertion site for the therapeutic peptide.

12. The method of claim 1, wherein the first genetic circuit or second genetic circuit further comprises one or more repressor proteins, wherein the one or more repressor proteins is LacI, TetR, and/or QS.

13. The method of claim 3, wherein the platelets or red blood cells express one or more cell surface markers, wherein the one or more cell surface markers are CD41a and CD42b.

14. The method of claim 1, wherein the genetically engineered fed cell is derived from an embryonic stem cell or a mouse embryonic stem cell; or is a hematopoietic progenitor stem cell, wherein the hematopoietic progenitor stem cell is derived from cord blood, bone marrow, iPScell, or ES cell.

* * * * *

SEQUENCE LISTING

```
<160> NUMBER OF SEQ ID NOS: 1

<210> SEQ ID NO 1
<211> LENGTH: 4
<212> TYPE: PRT
<213> ORGANISM: Artificial Sequence
<220> FEATURE:
<223> OTHER INFORMATION: Synthetic construct

<400> SEQUENCE: 1

Leu Lys Asn Gly
1
```